(12) United States Patent
Sumino

(10) Patent No.: US 6,331,602 B1
(45) Date of Patent: Dec. 18, 2001

(54) MONOMER AND A POLYMER OBTAINED THEREFROM

(75) Inventor: Motoshige Sumino, Saitama (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/656,458

(22) Filed: Sep. 6, 2000

Related U.S. Application Data

(62) Division of application No. 09/195,237, filed on Nov. 18, 1998, now Pat. No. 6,160,068.

(30) Foreign Application Priority Data

Nov. 19, 1997 (JP) ................................................. 9-335055

(51) Int. Cl.⁷ ..................................................... C08F 10/00
(52) U.S. Cl. ......................... 526/281; 526/282; 526/284; 526/285; 526/303.1; 526/308; 526/309; 526/310; 526/319; 526/332; 526/347.1
(58) Field of Search .................................... 526/281, 282, 526/284, 285, 303.1, 308, 309, 310, 319, 332, 347.1

(56) References Cited

U.S. PATENT DOCUMENTS 5,059,698  * 10/1991  Schulthess et al. .................. 549/375
5,621,019     4/1997  Nakano ................................. 522/49

FOREIGN PATENT DOCUMENTS 0 347 381 A1   12/1989  (EP) .
0 875 496 A1   11/1998  (EP) .

OTHER PUBLICATIONS

Choi et al., J. Photopolym. Sci. Technol. (1997). 10(3), 521–528.*
Choi et al. Proc. SPIE–Int. Soc. Opt. Eng. (1997), 3049, 104–112.*

* cited by examiner

*Primary Examiner*—Helen L. Pezzuto
(74) *Attorney, Agent, or Firm*—Armstrong, Westerman, Hattori, McLeland & Naughton, LLP

(57) ABSTRACT

This invention relates to a monomer shown by the general formula [1]

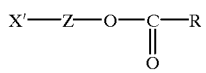

(wherein X' is a cyclic hydrocarbon residue containing polymerizable double bond(s), which may have a substituent, Z is a spacer or a direct bond and R is a substituted alkyl or alkenyl group having one or two protected hydroxyl groups as substituent) and a polymer containing a segment derived from the above monomer.

The said polymer is useful for a resist composition, etc. utilized in the production of semiconductor elements, etc. and the said monomer is useful as a starting material for the polymer, and a resist composition using the said polymer can remarkably advantageously be used as a resist material for ArF excimer laser beams which has been considered to be a valuable technology for exposure belonging to the coming generation.

7 Claims, No Drawings

MONOMER AND A POLYMER OBTAINED THEREFROM

This application is a division of prior application Ser. No. 09/195,237 filed Nov. 18, 1998 now U.S. Pat. No. 6,160,068.

BACKGROUND OF THE INVENTION

As alkaline soluble resins, there have heretofore been known novolac resin, phenolic resin, and polymers having acrylic acid or methacrylic acid as a structural component, and they have been used in photo prints and as the resist materials for electronics industries, and among them many polymers have been put into practical use. The following is typical examples; UV lights including g-line light (wavelength of 436 nm) and i-line light (wavelength of 365 nm) have been used as an exposure source in lithography field and further excimer laser beams (KrF excimer laser beams; wavelength of 248 nm and ArF excimer laser beams; wavelength of 193 nm) has recently been used for this purpose, and as the base polymers of the resist materials in accordance with the exposure source, novolac resin is mainly used as resist materials for g-line light and i-line light and phenolic resin is mainly used as resist materials for KrF, and both of those resins contain phenolic hydroxy groups (pKa of about 12) as functional groups which can be developed by an alkaline developing solution.

On the other hand, an acrylic acid derivative type or a methacrylic acid derivative type resins have mainly been used as a base polymer of ArF resist materials which have still been under developing stage (For instance, Japanese Patent Application Kokai (Laid-Open) Nos. (JP-A-) 7-199467, JP-A-8-82925 and JP-A-7-234511). The reason is that resins having aromatic rings so far being used is low in their transparency in far ultraviolet range and particularly it becomes completely non-transparent at the wavelength of ArF excimer laser beams, i.e. 193 nm. However, those resist materials wherein acrylic acid resin or methacrylic acid resin is used as the base polymer show high acidity (pKa of about 5) because a carboxylic group is used as a soluble group, which results in higher dissolving speed upon the development by alkaline substance as compared with known polymer wherein phenol groups are used as a soluble group, and therefore those resist materials are accompanied with such defects that a film is peeled off upon fine pattern formation and even non-exposured parts are dissolved out when a known alkaline developing solution, 2.38% tetramethylammonium hydroxide (TMAH), is used without diluting and thus no good pattern can be obtained.

Further, the main alkaline developing solution so far applied in actual production lines of semiconductor apparatuses is the above mentioned 2.38% TMAH, and it is actually very difficult to use the developing solution in diluted state in the production lines wherein resist materials belonging to different generations, such as both of i-line lights resist and KrF resist and both of KrF resist and ArF resist are applied together.

SUMMARY OF THE INVENTION

The present invention has been accomplished taking into consideration the above mentioned circumstances and has the object to provide a novel polymer showing high transmittance against deep-ultraviolet lights having a wavelength of 220 nm or less, particularly ArF excimer laser beams, which can give, upon using, for instance, as a polymer for a resist composition, a resist film showing high etching resistance and to provide a novel monomer usable as a starting material of the said polymer.

The present invention relates to a novel polymer useful as a resist composition used in the production of semiconductor elements and so on and to a novel monomer useful as a starting material of the said polymer.

More particularly, the present invention relates to a monomer shown by the general formula [1]

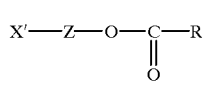

[1]

(wherein X' is a cyclic hydrocarbon residue containing polymerizable double bond(s), which may have a substituent, Z is a spacer or a direct bond and R is a substituted alkyl or alkenyl group having one or two protected hydroxyl groups as substituent).

Further, the present invention relates to a polymer, which contains, as a constituent unit, a monomer unit shown by the general formula [1a]

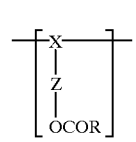

[1a]

(wherein X is a cyclic hydrocarbon residue which may have a substituent, and Z and R have the same meaning as above).

DETAILED DESCRIPTION OF THE PREFERRED EMBODIMENTS

For the purpose of attaining the above mentioned objects, the present inventors have extensively studied to find out a novel polymer containing, as a structural unit, a monomer unit shown by the above general formula [1a] having high transmittance in a wavelength region of 220 nm or less, which can give, upon using a resist material, a resist film showing high etching resistance, and the present invention has been accomplished on the basis of this finding.

The cyclic hydrocarbon residue containing polymerizable double bond(s), which may have a substituent, shown by X' in the general formula [1] includes cyclic groups shown by the following general formulae [2] to [4]

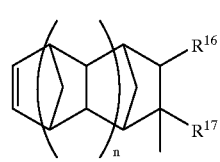

[2]

(wherein $R^{16}$ and $R^{17}$ are each independently a hydrogen atom, an alkyl group, a cyano group, an alkyloxycarbonyl group, an aryl group, an aralkyl group or a carbamoyl group, and n is 0 or 1),

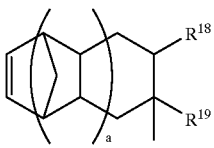

[3]

(wherein $R^{18}$ and $R^{19}$ are each independently a hydrogen atom, an alkyl group, a cyano group, an alkyloxycarbonyl group, an aryl group, an aralkyl group or a carbamoyl group, and 'a' is 0 or 1),

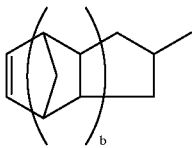

[4]

(wherein b is 0 or 1).

The cyclic hydrocarbon residue which may have a substituent, shown by X in the general formula [1a] is derived from the cyclic hydrocarbon residue containing polymerizable double bond(s), which may have a substituent, shown by X' in the general formula [1], and it includes the groups shown by the following general formulae [2a] to [4a]

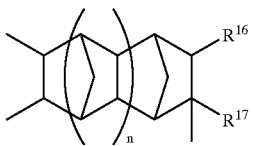

[2a]

(wherein $R^{16}$, $R^{17}$ and n have the same meaning as above),

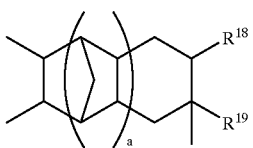

[3a]

(wherein $R^{18}$, $R^{19}$ and 'a' have the same meaning as above),

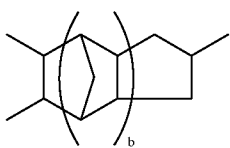

[4a]

(wherein b has the same meaning as above).

The alkyl group shown by $R^{16}$ to $R^{19}$ may be straight chained, branched or cyclic, and includes one having 1 to 20 carbon atoms, which is specifically exemplified by a methyl group, an ethyl group, a n-propyl group, an isopropyl group, an n-butyl group, an isobutyl group, a tert-butyl group, a sec-butyl group, an n-pentyl group, an isopentyl group, a neopentyl group, a tert-pentyl group, a 3,3-dimethylbutyl group, a 1,1-dimethylbutyl group, a 1-methylpentyl group, an n-hexyl group, an isohexyl group, a heptyl group, an octyl group, a nonyl group, a decyl group, an undecyl group, a dodecyl group, a hexadecyl group, an octadecyl group, a 2-ethylhexyl group, a cyclopropyl group, a cyclopentyl group, a cyclohexyl group, etc.

The alkyloxycarbonyl group may be straight chained, branched or cyclic.

The straight chained or branched one includes one having 2 to 19 carbon atoms, which is specifically exemplified by a methyloxycarbonyl group, an ethyloxycarbonyl group, a propyloxycarbonyl group, a butyloxycarbonyl group, a pentyloxycarbonyl group, a hexyloxycarbonyl group, a heptyloxycarbonyl group, an octyloxycarbonyl group, a dodecyloxycarbonyl group, an octadecyloxycarbonyl group, a tert-butyloxycarbonyl group, a 2-ethylhexyloxycarbonyl group, etc.

The cyclic one may be monocyclic or polycyclic and includes alicyclic one having 6 to 14 carbon atoms, which is specifically exemplified by a cyclohexyloxycarbonyl group, a tricyclodecanyloxycarbonyl group, an adamantyloxycarbonyl group, a norbornyloxycarbonyl group, a bicyclo[3.2.1]octenyloxycarbonyl group, a bicyclo[2.2.2]octyloxycarbonyl group, a mentyloxycarbonyl group, an isobornyloxycarbonyl group, etc.

The aryl group is specifically exemplified by a phenyl group, a tolyl group, a xylyl group, a naphthyl group, a trimethylphenyl group, etc.

The aralkyl group includes one having 7 to 15 carbon atoms, which is specifically exemplified by a benzyl group, a phenethyl group, a naphthylmethyl group, etc.

The cyclic hydrocarbon residue containing polymerizable double bond(s) which may have a substituent, shown by X' in the general formula [1] includes a monocyclic hydrocarbon residue, which is specifically examplified by a 3-cyclopenten-1-yl group, a 3-cyclohexene-1-yl group, etc.; a dicyclic hydrocarbon residue, which is specifically exemplified by a bicyclo[2.2.1]hept-2-en-5-yl group, a 1-methylbicyclo[2.2.1]hept-2-en-5-yl group, a 5-methylbicyclo[2.2.1]hept-2-en-5-yl group, a 7-methylbicyclo[2.2.1]hept-2-en-5-yl group, a 1-ethylbicyclo[2.2.1]hept-2-en-5-yl group, a 5-ethylbicyclo[2.2.1]hept-2-en-5-yl group, a 5-isopropylbicyclo[2.2.1]hept-2-en-5-yl group, a 5-pentylbicyclo[2.2.1]hept-2-en-5-yl group, a 5-heptylbicyclo[2.2.1]hept-2-en-5-yl group, a 5-(2-ethylhexyl)bicyclo[2.2.1]hept-2-en-6-yl group, a 7-octylbicyclo[2.2.1]hept-2-en-5-yl group, a 1-nonylbicyclo[2.2.1]hept-2-en-5-yl group, a 5-nonylbicyclo[2.2.1]hept-2-en-5-yl group, 5-dodecylbicyclo[2.2.1]hept-2-en-5-yl group, a 5-pentadecylbicyclo[2.2.1]hept-2-en-5-yl group, a 5,5-dimethylbicyclo[2.2.1]hept-2-en-6-yl group, a 1,4-diisopropylbicyclo[2.2.1]hept-2-en-5-yl group, a 5,5-diisopropylbicyclo[2.2.1]hept-2-en-6-yl group, a 5,5-dibutylbicyclo[2.2.1]hept-2-en-6-yl group, a 5,5-dihexylbicyclo[2.2.1]hept-2-en-6-yl group, a 5-methyl-5-ethylbicyclo[2.2.1]hept-2-en-6-yl group, a 5,5-didecylbicyclo[2.2.1]hept-2-en-6-yl group, a 5,6-dimethylbicyclo[2.2.1]hept-2-en-5-yl group, a 5-methyl-6-ethylbicyclo[2.2.1]hept-2-en-5-yl group, a 5,6-dipropylbicyclo[2.2.1]hept-2-en-5-yl group, a 5,6-diisopropylbicyclo[2,2,1]hept-2-en-5-yl group, a 5,6-dipentylbicyclo[2.2.1]hept-2-en-5-yl group, a 5,6-di(2-ethylhexyl) bicyclo[2.2.1]hept-2-en-5-yl group, a 5,6-didodecylbicyclo[2.2.1]hept-2-en-5-yl group, a 5,5,6-trimethylbicyclo[2.2.1]hept-2-en-6-yl group, a 1-phenylbicyclo[2.2.1]hept-2-en-5-yl group, a 5-phenylbicyclo[2.2.1]hept-2-en-6-yl group, a 7-phenylbicyclo[2.2.1]hept-2-en-5-yl group, a 5-naphthylbicyclo[2.2.1]hept-2-en-6-yl group, a 5,5-diphenylbicyclo[2.2.1]hept-2-en-6-yl group, a 5,6-diphenylbicyclo[2.2.1]hept-2-en-5-yl group, a 2-benzylbicyclo[2.2.1]hept-2-en-5-yl group, a 5-benzylbicyclo[2.2.1]hept-2-en-5-yl group, a 5-phenethylbicyclo[2.2.1]hept-2-en-5-yl group, a 5,6-dibenzylbicyclo[2.2.1]hept-2-en-5-yl group, a 5-α-methylbicyclo[2.2.1]hept-2-en-5-yl group, a 5-naphthylbicyclo[2.2.1]hept-2-en-5-yl group, a 5-tolylbicyclo[2.2.1]hept-2-en-5-yl group, a 5,6-ditolylbicyclo[2.2.1]hept-2-en-5-yl group, a 5-xylylbicyclo[2.2.1]hept-2-en-5-yl group, a 5-methylnaphthylbicyclo[2.2.1]hept-2-en-5-yl group, a 5-cyclobutylbicyclo[2.2.1]hept-2-en-5-yl group, a 5,6-dicyclopentylbicyclo[2.2.1]hept-2-en-5-yl group, a 5-methylcyclopentylbicyclo[2.2.1]hept-2-en-5-yl group, a 5-isopropylcyclopentylbicyclo[2.2.1]hept-2-en-5-yl group, a 5-cyclohexylbicyclo[2.2.1]hept-2-en-5-yl group, etc.; a tricyclic hydrocarbon residue which is specifically exemplified by a tricyclo[$5.2.1.0^{2.6}$]dec-8-en-3-yl group, a tricyclo[$5.2.1.0^{2.6}$]dec-8-en-4-yl group, a 3-methyltricyclo[$5.2.1.0^{2.6}$]dec-8-en-4-yl group, a 3-ethyltricyclo[$5.2.1.0^{2.6}$]dec-8-en-4-yl group, a 3,5-dimethyltricyclo[$5.2.1.0^{2.6}$]dec-8-en-4-yl group, etc. and a tetracyclic hydrocarbon residue which is specifically exemplified by a tetracyclo[$4.4.0.1^{2.5}.1^{7.10}$]dodec-3-en-8-yl group, etc.

When the polymer obtained by polymerization of the monomer of the present invention shown by the general formula [1] is used as an ArF resist material, the above cyclic hydrocarbon shown by X' is preferably the polycyclic hydrocarbon residue such as the dicyclic hydrocarbon residue, the tricyclic hydrocarbon residue and the tetracyclic hydrocarbon residue, among which those containing no aromatic group are more preferable.

The substituted alkyl or alkenyl group having one or two protected hydroxyl groups as substituent, shown by R in the general formula [1] and [1a] may be straight chained, branched or cyclic, and includes one shown by the following general formula [5] or [6]

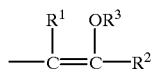

[5]

(wherein $R^1$ and $R^2$ are each independently a hydrogen atom, an alkyl group, a substituted alkyl group or an alicyclic hydrocarbon residue, and $R^1$ and $R^2$ may form together an aliphatic ring, and $R^3$ is an alkyl group, an alkenyl group, a hydroxyalkyl group, an alkyloxycarbonyl group or an alkylsilyl group)

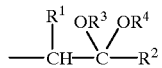

[6]

(wherein $R^4$ is an alkyl group and $R^1$, $R^2$ and $R^3$ have the same meaning as above, and $R^3$ and $R^4$ may form together an aliphatic ring).

The alkyl group shown by $R^1$ and $R^2$ in the general formulae [5] and [6] may be straight chained, branched or cyclic and includes one having 1 to 12 carbon atoms, preferably 1 to 8 carbon atoms, which is specifically exemplified by a methyl group, an ethyl group, an n-propyl group, an isopropyl group, an n-butyl group, an isobutyl group, a tert-butyl group, a sec-butyl group, an n-pentyl group, an isopentyl group, a neopentyl group, a tert-pentyl group, a 3,3-dimethylbutyl group, a 1,1-dimethylbutyl group, a 1-methylpentyl group, an n-hexyl group, an isohexyl group, an n-heptyl group, an isoheptyl group, an n-octyl group, an isooctyl group, a 2-ethylhexyl group, a cyclopropyl group, a cyclopentyl group, a cyclohexyl group, a 2-cyclohexylethyl group, etc.

The case where $R^1$ and $R^2$ in the general formula [5] form together an aliphatic ring includes one where they form together the aliphatic ring composed of an alkylene chain having 3 to 10 carbon atoms.

The aliphatic ring may be monocyclic or polycyclic.

The specific example of the aliphatic ring includes 2-norbornene, cyclopentene, cyclohexene, cyclooctene, cyclodecene, etc.

The case where $R^1$ and $R^2$ in the general formula [6] form together an aliphatic ring includes one where they form together the aliphatic ring composed of an alkylene chain having 3 to 10 carbon atoms.

The aliphatic ring may be monocyclic or polycyclic.

The specific example of the aliphatic ring includes 2-norbornane, cyclopentane, cyclohexane, cyclooctane, cyclodecane, etc.

The substituted alkyl includes one having 1 to 12 carbon atoms, preferably 1 to 8 carbon atoms wherein at least one hydrogen atoms of the above alkyl group are substituted by a cyano group, a hydroxy group, a halogen atom such as fluorine, chlorine, bromine and iodine, a lower alkoxy group having 1 to 6 carbon atoms such as a methoxy group, an ethoxy group, a propoxy group, an isopropoxy group, a butoxy group, a tert-butoxy group, a pentyloxy group and a hexyloxy group or other functional group, which is specifically exemplified by a cyanoalkyl group such as a cyanomethyl group, a cyanoethyl group, a cyanopropyl group, a cyanobutyl group, a cyanopentyl group, a cyanohexyl group and a cyanoheptyl group; a hydroxyalkyl group such as a hydroxyemthyl group, a hydroxyethyl group, a hydroxypropyl group, a hydroxybutyl group, a hydroxypentyl group, a hydroxyhexyl group, a hydroxyheptyl group and a hydroxyoctyl group; a haloalkyl group such as a chloromethyl group, a bromomethyl group, a trifluoromethyl group, a 2-chloroethyl group, a 3-chloropropyl group, a 3-bromopropyl group, a 3,3,3-trifluoropropyl group and a perfluorooctyl group; an alkoxyalkyl group such as a methoxymethyl group, a methoxyethyl group, an ethoxymethyl group, an ethoxyethyl group, a propoxymethyl group, a 2-propoxymethyl group, a propoxyethyl group, a butoxymethyl group and a tert-butoxymethyl group, etc.

The alicyclic hydrocarbon residue includes one having 3 to 30 carbon atoms, preferably 5 to 12 carbon atoms, which is specifically exemplified by a tricyclo[$5.2.1.0^{2.6}$]decanyl group, a dicyclopentenyl group, an adamantyl group, a norbornyl group, an isobornyl group, a 2-methyl-2-adamantyl group, a mentyl group, etc.

The alkyl group shown by $R^3$ may be straight chained or branched and includes one having 1 to 12 carbon atoms, preferably 1 to 8 carbon atoms, which is specifically exemplified by a methyl group, an ethyl group, an n-propyl group, an isopropyl group, an n-butyl group, an isobutyl group, a tert-butyl group, a sec-butyl group, an n-pentyl group, an isopentyl group, a neopentyl group, a tert-pentyl group, a 3,3-dimethylbutyl group, a 1,1dimethylbutyl group, a 1-methylpentyl group, a n-hexyl group, an isohexyl group, an n-heptyl group, an isoheptyl group, an n-octyl group, an isooctyl group, a 2-ethylhexyl group, etc.

The alkenyl group may be straight chained or branched and include one having 2 to 12 carbon atoms, preferably 2 to 8 carbon atoms, which is specifically exemplified by an ethenyl group, a propenyl group, an isopropenyl group, a butenyl group, an isobutenyl group, a pentenyl group, an isopentenyl group, a hexenyl group, an isohexenyl group, a heptenyl group, an octenyl group, etc.

The hydroxyalkyl group may be straight chained or branched and includes one having 1 to 12 carbon atoms, preferably 2 to 8 carbon atoms, which is specifically exemplified by a hydroxyethyl group, a hydroxypropyl group, a hydroxybutyl group, a hydroxypentyl group, a hydroxyhexyl group, a hydroxyheptyl group, a hydroxyoctyl group, etc.

The alkyloxycarbonyl group may be straight chained, branched or cyclic and includes one having 2 to 19 carbon atoms, which is specifically exemplified by an ethyloxycarbonyl group, a propyloxycarbonyl group, a butyloxycarbonyl group, a pentyloxycarbonyl group, a hexyloxycarbonyl group, a heptyloxycarbonyl group, an octyloxycarbonyl group, a dodecyloxycarbonyl group, an octadecyloxycarbonyl group, a tert-butyloxycarbonyl group, a 2-ethylhexyloxycarbonyl group, a cyclohexyloxycarbonyl group, etc.

The alkyl group in the alkylsilyl group may be straight chained or branched and include a lower alkyl group having 1 to 6 carbon atoms, which is specifically exemplified by a methyl group, an ethyl group, an n-propyl group, an isopropyl group, an n-butyl group, an isobutyl group, a tert-butyl group, a sec-butyl group, an n-pentyl group, an isopentyl group, a neopentyl group, a tert-pentyl group, a 3,3-dimethylbutyl group, a 1,1-dimethylbutyl group, a 1-methylpentyl group, an n-hexyl group, an isohexyl group, etc. The alkylsilyl group includes preferably a trialkylsilyl group such as a trimethylsilyl group, a triethylsilyl group, a tri-n-propylsilyl group, a triisopropylsilyl group, a tri-n-butylsilyl group, a tripentylsilyl group, a tri-n-hexylsilyl group and a tert-butyldimethylsilyl group.

The alkyl group shown by $R^4$ in the general formula [6] may be straight chained or branched and includes one having 1 to 12 carbon atoms, preferably 1 to 8 carbon atoms, which is specifically exemplified by a methyl group, an ethyl group, an n-propyl group, an isopropyl group, an n-butyl group, an isobutyl group, a tert-butyl group, a sec-butyl group, an n-pentyl group, an isopentyl group, a neopentyl group, a tert-pentyl group, a 3,3-dimethylbutyl group, a 1,1-dimethylbutyl group, a 1-methylpentyl group, an n-hexyl group, an isohexyl group, an n-heptyl group, an isoheptyl group, an n-octyl group, an isooctyl group, a 2-ethylhexyl group, etc.

The case where $R^3$ and $R^4$ form together an aliphatic ring includes one where they form together a ring containing an alkylene chain having 2 to 10 carbon atoms, and the ring may be monocyclic or polycyclic. The alkylene chain may contain a hydroxy group, or may contain —O— group at its optional position in the chain, or may contain a double bond at its optional position in the main or side chain. The alkylene chain may be straight chained or branched and includes specifically an ethylene group, a propylene group, an isopropylene group, an isopropylidene group, a butylene group, a 2-methylpropylene group, a pentylene group, a 2,2-dimethylpropylene group, a 2-ethylpropylene group, a hexylene group, a 2-butyl-2-ethylpropylene group, an ethenylene group, a propenylene group, a butenylene group, a vinylidene group, a group of —CH$_2$C(=CH$_2$)CH$_2$—, a 1-hydroxyethylene group, a 2-hydroxypropylene group, a 2-hydroxybutylene group, a 2-hydroxypentylene group, a 3-hydroxypentylene group, a 2-hydroxyhexylene group, a 3-hydroxyhexylene group, a group of —CH$_2$—O—CH$_2$—, a group of —CH$_2$CH$_2$—O—CH$_2$—, a group of —CH$_2$CH$_2$—O—CH$_2$CH$_2$—, etc., among which one having 2 to 4 carbon atoms is preferable.

Among the substituted alkyl or alkenyl group having one or two protected hydroxyl groups as substituent shown by R, those shown by the following general formula [7], [8] or [8'] are preferable

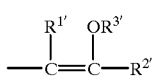

[7]

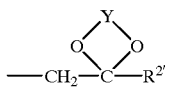

[8]

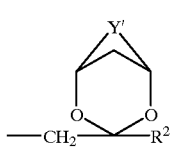

[8']

(wherein $R^{1'}$ is a hydrogen atom, $R^{2'}$ and $R^{3'}$ are a lower alkyl group having 1 to 4 carbon atoms and $R^{1'}$ and $R^{2'}$ may form together a lower alkylene group having 3 to 4 carbon atoms and Y and Y' are a group shown by the formula [9] or the general formula [10]

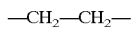

—CH$_2$—CH$_2$— [9]

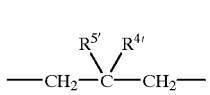

[10]

in which $R^{4'}$ and $R^{5'}$ are a hydrogen atom or a lower alkyl group having 1 to 4 carbon atoms).

The spacer shown by Z includes one shown by the following general formula [11].

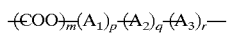

—(COO)$_{\overline{m}}$(A$_1$)$_p$—(A$_2$)$_q$—(A$_3$)$_r$— [11]

(wherein A$_2$ is a divalent hydrocarbon residue which may contain an oxygen atom, A$_1$ and A$_3$ are each independently a lower alkylene group, m, p, q and r are each independently 0 or 1, provided that q is 1 when m is 1, and at least one of m, p, q and r is 1.)

The divalent hydrocarbon group which may contain an oxygen atom shown by A$_2$ in the general formula [11] includes an alkylene group and a divalent aromatic group.

The alkylene group may be straight chained, branched or cyclic and includes one having 1 to 20 carbon atoms such as a methylene group, an ethylene group, a propylene group, a butylene group, a 2-methylpropylene group, a pentylene group, 2,2-dimethylpropylene group, 2-ethylpropylene group, a hexylene group, a heptylene group, an octylene group, a 2-ethylhexylene group, a nolylene group, a decylene group, a cyclopropylene group, a cyclopentylene group, a cyclohexylene group, an adamantanediyl group, a tricyclo[5,2,1,0$^{2,6}$]decanediyl group, a norbornanediyl group, a methylnorbornanediyl group, an isobornanediyl group and a decalinediyl group, and the divalent aromatic group includes an o-phenylene group, a m-phenylene group, a p-phenylene group, a diphenylene group, a p-xylene-α, α'-diyl group, etc. among which an alkylene group having 1 to 10 carbon atoms is preferable.

The case wherein the divalent hydrocarbon group contains an oxygen group includes one wherein 1 or more, preferably 1 to 3 oxygen atoms are contained in the main chain and/or the side chain of the divalent hydrocarbon group, typical examples of which are a methoxyethylethylene group, an ethoxyethylethylene group, a bornyloxyethylethylene group, a norbornyloxyethylethylene group, a mentyloxyethylethylene group, an adamantyloxyethylethylene group, a methoxyethoxyethylethylene group, an ethoxyethoxyethylethylene group, a bornyloxyethoxyethylethylene group, a mentyloxyethoxyethylethylene group, a group of —O—CH$_2$—, a group of —O—CH$_2$—CH$_2$—, a group of —CH$_2$—O—CH$_2$—, a group of —CH$_2$—CH$_2$—O—CH$_2$—, a group of —CH$_2$—CH$_2$—O—CH$_2$—CH$_2$—, a group of —CH$_2$—CH$_2$—O—CH$_2$—CH$_2$—O—CH$_2$—CH$_2$—, a group of —CH$_2$—O—C$_6$H$_4$—, etc.

The lower alkylene group shown by A$_1$ and A$_3$ may be straight chained or branched and includes one having 1 to 6 carbon atoms such as a methylene group, an ethylene group, a propylene group, a butylene group, a 2-methylpropylene group, a pentylene group, a 2,2-dimethylpropylene group, a 2-ethylpropylene group and a hexylene group.

Among the spacer shown by Z, those shown by the following general formula [12] are preferable.

[12]

(wherein m' and p' are each independently 0 or 1, provided that at least one of m' and p' are 1).

The monomer unit shown by the above general formula [1a] of the present invention is one derived from the monomer shown by the above general formula [1].

When the polymer containing the monomer unit shown by the above general formula [1a] of the present invention is used as an ArF resist material, the polymer is preferably one containing no aromatic group.

Typical examples thereof are as follows.

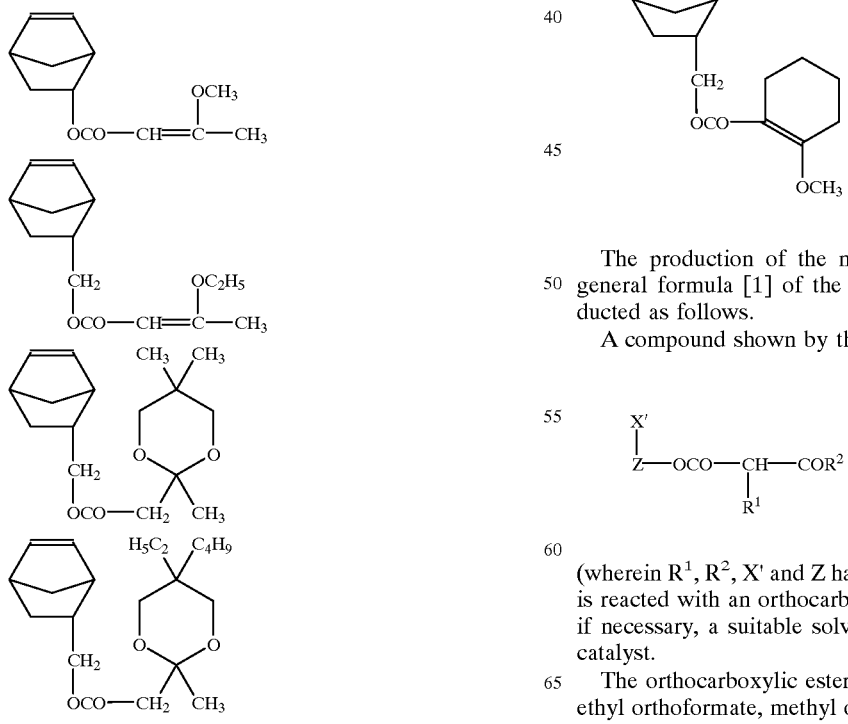

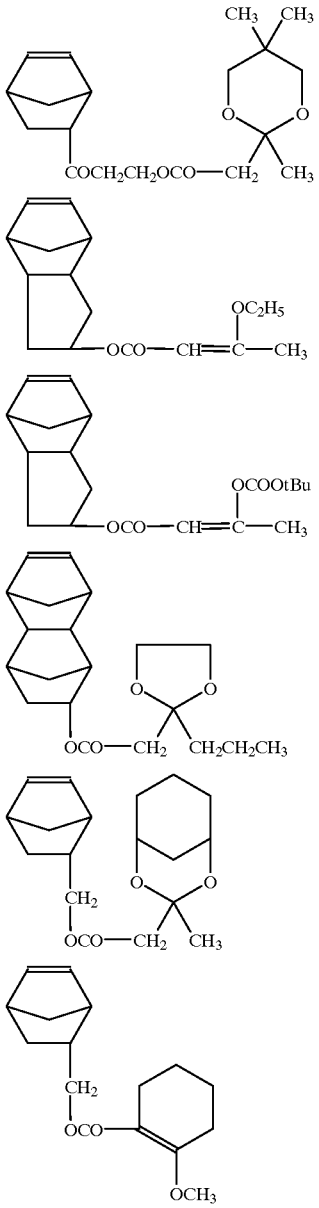

The production of the monomer shown by the above general formula [1] of the present invention can be conducted as follows.

A compound shown by the general formula [13]

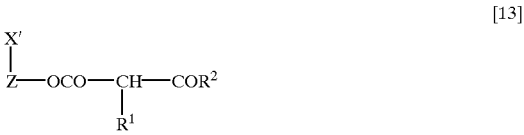
[13]

(wherein R$^1$, R$^2$, X' and Z have the same meaning as above) is reacted with an orthocarboxylic ester in the presence of, if necessary, a suitable solvent in the presence of an acid catalyst.

The orthocarboxylic ester includes methyl orthoformate, ethyl orthoformate, methyl orthoacetate, ethyl orthoacetate, etc.

An amount of the orthocarboxylic ester to be used is not specifically limited and can be suitably selected, and generally 1 to 30 times mole, preferably 1 to 10 times mole, relative to the compound shown by the general formula [13].

The acid catalyst includes an organic acid (or its salt) such as camphor sulfonic acid, p-toluene sulfonic acid, pyridinium p-toluene sulfonate, oxalic acid and pyridinium chloride; an inorganic acid such as hydrochloric acid, sulfuric acid and nitric acid; Lewis acid such as aluminum chloride, boron trifluoride diethylether complex ($BF_3.Et_2O$), etc.

An amount of the acid catalyst is not specifically limited and can suitably be selected, and generally 0.1 to 20 mole %, preferably 1 to 10 mole % of the compound shown by the general formula [13].

The solvent, which is used upon necessity, includes a hydrocarbon such as toluene, xylene, benzene, cyclohexane, n-hexane and n-octane; a halogenated hydrocarbon such as methylene chloride, dichloroethane, trichloroethylene, carbon tetrachloride and chloroform; an ester such as methyl acetate, ethyl acetate, n-butyl acetate and methyl propionate; an alcohol such as methanol, ethanol, n-propanol, isopropanol, n-butanol, isobutanol and tert-butanol; an ether such as dimethylether, diethylether, diisopropylether, dimethoxyethane, tetrahydrofuran and dioxane, N-methylpyrrolidone; N,N-dimethylformamide, N,N-dimethylacetamide, dimethylsulfoxide, etc. The solvent may be used alone or in suitable combination of two or more thereof.

The reaction temperature is not specifically limited and selected from a range of generally 0 to 150° C., preferably 20 to 80° C.

The reaction time is variable depending upon the kind of the compound shown by the above general formula [13] and concentration and other reaction conditions and is selected from a range of generally 0.5 to 10 hours.

The monomer shown by the above general formula [1] of the present invention can also be prepared by the following method.

The compound shown by the above general formula [13] is reacted with a diol in the presence of, if necessary, a suitable solvent and in the presence of an acid catalyst.

The diol includes ethylene glycol, propylene glycol, 2,2-dimethylpropane diol, 1,3-butane diol, 1,4-butane diol, diethylene glycol, dipropylene glycol, neopentyl glycol, 1,6-hexane diol, 2,2,4-trimethyl-1,6-hexane diol, triethylene glycol, 2-butyl-2ethyl-1,3-propane diol, 1,2-cyclohexane diol, 1,3-cyclohexane diol, etc.

An amount of the diol to be used is suitably determined without specific limitation and selected from a range of generally 1 to 20 times mole, preferably 3 to 10 times mole, relative to the compound shown by the general formula [13].

The acid catalyst includes an organic acid (or its salt) such as camphor sulfonic acid, p-toluene sulfonic acid and pyridinium p-toluene sulfonate; an inorganic acid such as hydrochloric acid, sulfuric acid and phosphoric acid.

An amount of the acid catalyst to be used is suitably determined without specific limitation and selected from a range of generally 0.1 to 20 mole %, preferably 1 to 10 mole % of the compound shown by the general formula [13].

The solvent, which is used upon necessity, includes a hydrocarbon such as toluene, xylene, benzene, cyclohexane, n-hexane and n-octane; a halogenated hydrocarbon such as methylene chloride, dichloroethane, trichloroethylene, carbon tetrachloride and chloroform; an ester such as methyl acetate, ethyl acetate, n-butyl acetate and methyl propionate; an ether such as dimethylether, diethylether, diisopropylether, dimethoxyethane, tetrahydrofuran and dioxane; N-methylpyrrolidone, N,N-dimethylformamide, N,N-dimethylacetamide, dimethylsulfoxide, etc. The solvent may be used alone or in suitable combination of two or more thereof.

Among those solvents, preferable examples are those which can form an azeotropic mixture with water and thus can remove water from the reaction system.

The reaction temperature is not specifically limited and selected from a range of generally 0 to 150° C., preferably 20 to 130° C.

The reaction time is variable depending upon the kind of the compound shown by the above general formula [13] and concentration and other reaction conditions and is selected from a range of generally 0.5 to 48 hours.

The treatment after the reaction in the above two methods can be conducted according to a known method so far being used. The monomer shown by the above general formula [1] obtained above can be directly subjected to a polymerization reaction without purification and/or separation (namely, non-reacted compound shown by the above general formula [13] may coexist), or it can be subjected to the next reaction step after purification and/or separation by extraction, recrystallization or other suitable means.

As the compound shown by the above general formula [13], a commercially available one or one prepared by a known method can be used.

When the monomer of the present invention is one containing an alkylsilyl group, those compounds can be prepared by reacting the monomer of the present invention, which is obtained by any of the above mentioned methods, with an alkylsilyl halide in a suitable solvent, if necessary, in the presence of a basic catalyst.

The alkylsilyl halide includes chlorotrimethylsilane, chlorotriethylsilane, chlorodimethylethylilane, chlorotripropylsilane, chlorotriisopropylsilane, chlorotributylsilane, chlorotrihexylsilane, butyl chlorodimethylsilane, etc.

An amount of the alkylsilyl halide to be used is suitably determined without specific limitation and selected from a range of generally 1 to 20 times mole, preferably 1 to 5 times mole, to the compound containing no alkylsilyl group, shown by the general formula [1].

The basic catalyst includes an organic amine such as triethylamine, diisopropylethylamine, N,N-dimethylaniline, piperidine, pyridine, 4-dimethylaminopyridine, 1,5-diazabicyclo[4.3.0]non-5-ene, 1,8-diazabicyclo[5.4.0] undec-7-ene, tri-n-butylamine and N-methylmorpholine; a metal hydride such as sodium hydride; a basic alkaline metal compound such as n-butyl lithium and tert-butyl lithium, etc.

An amount of the basic catalyst to be used is suitably determined without specific limitation and selected from a range of generally 0.1 to 20 times mole, preferably 1 to 5 times mole, relative to the compound containing no alkylsilyl group, shown by the general formula [1].

The solvent, which is used upon necessity, includes a hydrocarbon such as toluene, xylene, benzene, cyclohexane, n-hexane and n-octane; a halogenated hydrocarbon such as methylene chloride, dichloroethane, trichloroethylene, carbon tetrachloride and chloroform; an ester such as methyl acetate, ethyl acetate, n-butyl acetate and methyl propionate; an ether such as dimethylether, diethylether, diisopropylether, dimethoxyethane, tetrahydrofuran and dioxane; N-methylpyrrolidone, N,N-dimethylformamide, N,N-dimethylacetamide, dimethylsulfoxide, etc. The solvent may be used alone or in suitable combination of two or more thereof.

The reaction temperature is not specifically limited and selected from a range of generally 0 to 150° C., preferably 20 to 80° C.

The reaction time is variable depending upon the kind of the compound containing no alkylsilyl group, shown by the above general formula [1] and concentration and other reaction conditions and is selected from a range of generally 0.5 to 48 hours.

The treatment after the reaction in the above method can be conducted according to a known method so far being used. The monomer shown by the above general formula [1] containing an alkylsilyl group obtained above can be directly subjected to a polymerization reaction without purification and/or separation (namely, non-reacted compound shown by the above general formula [13] may coexist), or it can be subjected to the next reaction step after purification and/or separation by extraction, recrystallization or other suitable means.

The polymer of the present invention which contains as a constituent unit a monomer unit shown by the above general formula [1a] of the present invention includes one containing as the constituent unit at least one kind of the monomer unit of the present invention, and one containing as the constituent unit at least one kind of the monomer unit of the present invention and another kind of a monomer unit than that of the present invention (hereinafter abbreviated as "another monomer unit").

The "another monomer unit" includes one shown by the following general formula [14a] and [15a]

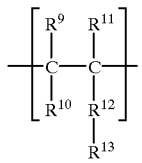

[14a]

(wherein $R^9$ is a hydrogen atom, a lower alkyl group or a halogen atom, $R^{10}$ is a hydrogen atom, a lower alkyl group, a halogen atom, a carboxyl group, an alkyloxycarbonyl group or a formyl group, $R^{11}$ is a hydrogen atom, a lower alkyl group, a carboxyl group, an alkyloxycarbonyl group or a halogen atom, $R^{12}$ is an alkylene group which may contain a double bond, or a direct bond, $R^{13}$ is a hydrogen atom, an alkyl group, a haloalkyl group, an aryl group which may have a substituent, an aliphatic heterocyclic group, an aromatic heterocyclic group, a halogen atom, an alkyloxycarbonyl group, an aralkyloxycarbonyl group, a hydroxyalkyloxycarbonyl group, an aryloxycarbonyl group, an acyloxy group, a cyano group, a carboxyl group, a formyl group, an amino group, a sulfonic acid residue, a carbamoyl group or a hydroxy group, and $R^{10}$ and $R^{13}$ may form together a group of —CO—Q—CO—{Q is O or N—$R^{14}$ [$R^{14}$ is a hydrogen atom, a lower alkyl group or a phenyl group]}).

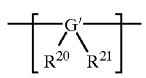

[15a]

(wherein G' is an aliphatic cyclic hydrocarbon residue, and $R^{20}$ and $R^{21}$ are each independently a hydrogen atom, an alkyl group, a group having hydrophilicity or an alkyloxycarbonyl group, and $R^{20}$ and $R^{21}$ may form together a dicarboximido group (—CO—NH—CO—)).

Among the group shown by the general formula [14a], those shown by the general formula [16] are preferable.

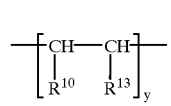

[16]

(in the general formula [16], $R^{10}$ and $R^{13}$ form together a group of —CO—Q—CO—{Q is O or N—$R^{14}$ [$R^{14}$ is a hydrogen atom or a lower alkyl group]}).

Among the group shown by the general formula [15a], those shown by the following general formulae [17] to [19] are preferable.

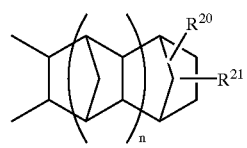

[17]

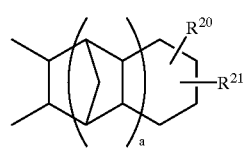

[18]

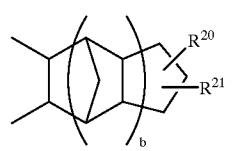

[19]

(wherein $R^{20}$ and $R^{21}$ have the same meaning as above and n, a and b are 0 or 1).

Further, the polymer of the present invention may contain, as a structural unit, a monomer unit shown by the general formula [13a] originated from the compound shown by the above general formula [13]

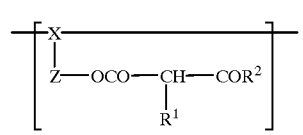

[13a]

(wherein $R^1$, $R^2$, X and Z have the same meaning as above).

The halogen atom shown by $R^9$, $R^{10}$, $R^{11}$ and $R^{13}$ in the general formula [14a] includes fluorine, chlorine, bromine and iodine.

The lower alkyl group shown by $R^9$, $R^{10}$, and $R^{11}$ may be straight chained or branched and includes one having 1 to 6 carbon atoms such as a methyl group, an ethyl group, an n-propyl group, an isopropyl group, an n-butyl group, an isobutyl group, a tert-butyl group, a sec-butyl group, an n-pentyl group, an isopentyl group, a neopentyl group, a tert-pentyl group, a 3,3-dimethylbutyl group, a 1,1-dimethylbutyl group, a 1-methylpentyl group, an n-hexyl group and an isohexyl group.

The alkyloxycarbonyl group shown by $R^{10}$, $R^{11}$ and $R^{13}$ may be straight chained, branched or cyclic and further it may contain a double bond. The straight chained or branched alkyloxycarbonyl group includes one having 2 to 19 carbon atoms such as a methyloxycarbonyl group, an ethyloxycarbonyl group, a propyloxycarbonyl group, a butyloxycarbonyl group, a pentyloxycarbonyl group, a hexyloxycarbonyl group, a heptyloxycarbonyl group, an octyloxycarbonyl group, a dodecyloxycarbonyl group, an octadecyloxycarbonyl group, an ethenyloxy carbonyl group, a propenyloxycarbonyl group, a butenyloxycarbonyl group, a tert-butyloxycarbonyl group and a 2-ethylhexyloxycarbonyl group. The cyclic alkyloxycarbonyl group may be a monocyclic or polycyclic one and includes an alicyclic alkyloxycarbonyl group having 6 to 14 carbon atoms, typical examples of which are a cyclohexyloxycarbonyl group, a tricyclodecanyloxycarbonyl group, an adamantyloxycarbonyl group, a norbornyloxycarbonyl group, a bicyclo[3.2.1]octenyloxycarbonyl group, a bicyclo[2.2.2]octyloxycarbonyl group, a mentyloxycarbonyl group, an isobornyloxycarbonyl group, etc.

The alkyl group shown by $R^{13}$ may be straight chained, branched or cyclic and includes one having 1 to 20 carbon atoms such as a methyl group, an ethyl group, an n-propyl group, an isopropyl group, an n-butyl group, an isobutyl group, a tert-butyl group, a sec-butyl group, an n-pentyl group, an isopentyl group, a neopentyl group, a tert-pentyl group, a 3,3-dimethylbutyl group, a 1,1-dimethylbutyl group, a 1-methylpentyl group, an n-hexyl group, an isohexyl group, an n-heptyl group, an octyl group, a nonyl group, a decyl group, an undecyl group, a dodecyl group, a hexadecyl group, an octadecyl group, 2-ethylhexyl group, a cyclopropyl group, a cyclopentyl group and a cyclohexyl group.

The haloalkyl group include one having 1 to 20 carbon atoms wherein the above alkyl group is halogenated (fluorinated, chlorinated, brominated or iodinated) such as a chloromethyl group, a bromomethyl group, a trifluoromethyl group, a 2-chloroethyl group, a 3-chloropropyl group, a 3-bromopropyl group, a 3,3,3-trifluoropropyl group, a 2-perfluorooctylethyl group, a perfluorooctyl group, a 1-chlorodecyl group, and a 1-chlorooctadecyl group.

The aryl group in the aryl group which may have a substituent includes one having 6 to 20 carbon atoms such as a phenyl group, a tolyl group, a xylyl group, a naphthyl group, an anthryl group, 4-ethylphneyl group, and 4-vinylphenyl group, and the substituent includes an alkoxy group having 1 to 6 carbon atoms such as a methoxy group, an ethoxy group, a propoxy group, a butoxy group, a pentyloxy group and a hexyloxy group; a halogen atom such as fluorine, chlorine, bromine and iodine; and an amino group.

The typical examples of the aryl group having a substituent are a 4-methoxyphenyl group, a 4-chlorophenyl group, a 4-aminophenyl group, and the like.

As the aliphatic heterocyclic group, 5- or 6-membered ones are preferable, and the group includes one containing 1 to 3 heteroatoms such as a nitrogen atom, an oxygen atom and a sulfur atom, typical examples of which are a pyrrolidinyl-2-one group, a piperidino group, a morpholino group, and the like.

As the aromatic heterocyclic group, 5- or 6-membered ones are preferable, and the group includes one containing 1 to 3 heteroatoms such as a nitrogen atom, an oxygen atom and a sulfur atom, typical examples of which are a pyridyl group, an imidazolyl group, a thiazolyl group, a furanyl group and a pyranyl group.

The aralkyloxycarbonyl group includes one having 8 to 20 carbon atoms such as a benzyloxycarbonyl group and a phenethyloxycarbonyl group.

The acyloxy group includes one having 2 to 18 carbon atoms which is derived from a carboxylic acid, such as an acetyloxy group, a propionyloxy group, a butylyloxy group, a pentanoyloxy group, a hexanoyloxy group, a heptanoyloxy group, an octanoyloxy group, a lauroyloxy group, a stearoyloxy group and a benzoyloxy group.

The hydroxyalkyloxycarbonyl group includes one having 2 to 19 carbon atoms wherein a hydrogen atom of the above mentioned alkyloxycarbonyl group is substituted with a hydroxy group, such as a hydroxymethyloxycarbonyl group, a hydroxyethyloxycarbonyl group, a hydroxypropyloxycarbonyl group, a hydroxybutyloxycarbonyl group, a hydroxypentyloxycarbonyl group, a hydroxyhexyloxycarbonyl group, a hydroxyheptyloxycarbonyl group, a hydroxyoctyloxycarbonyl group, a hydroxydodecyloxycarbonyl group and a hydroxyoctadecyloxycarbonyl group.

The aryloxycarbonyl group includes one having 7 to 15 carbon atoms as preferable examples, such as a phenyloxycarbonyl group and a naphthyloxycarbonyl group.

The alkylene group which may contain a double bond shown by $R^{12}$ may be straight chained or branched and includes one having 1 to 10 carbon atoms, and the group containing a double bond includes one containing 1 or more, preferably 1 to 5, more preferably 1 to 3 double bonds at the terminal or intermediate position(s) of the alkylene group.

The typical examples thereof are a methylene group, an ethylene group, a propylene group, a butylene group, a 2-methylpropylene group, a pentylene group, a 2,2-dimethylpropylene group, a 2-ethylpropylene group, a hexylene group, a heptylene group, an octylene group, a 2-ethylhexylene group, a nonylene group, a decylene group, an ethenylene group, a propenylene group, a butenylene group, a pentenylene group, a hexenylene group and a butadienylene group.

The lower alkyl group shown by $R^{14}$ in Q in the group of —CO—Q—CO— formed by binding $R^{10}$ and $R^{13}$ in the general formula [14a] may be straight chained, branched or cyclic and include one having 1 to 6 carbon atoms, which is specifically exemplified by a methyl group, an ethyl group, an n-propyl group, an isopropyl group, an n-butyl group, an isobutyl group, a tert-butyl group, a sec-butyl group, an n-pentyl group, an isopentyl group, a neopentyl group, a tert-pentyl group, a 3,3-dimethylbutyl group, a 1,1-dimethylbutyl group, 1-methylpentyl group, an n-hexyl group, an isohexyl group, a cyclopropyl group, a cyclopentyl group, a cyclohexyl group, etc.

The monomer unit shown by the general formula [14a] is originated from a monomer shown by the general formula [14]

[14]

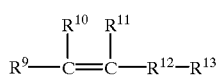

(wherein $R^9$ to $R^{13}$ have the same meaning as above).

The typical examples of the monomer are ethylenically unsaturated aromatic hydrocarbons having 8 to 20 carbon atoms such as styrene, 4-methylstyrene, 4-ethylstyrene, 4-methoxystyrene and divinylbenzene; alkenyl esters having 3 to 20 carbon atoms such as vinyl fornate, vinyl acetate, vinyl propionate and isopropenyl acetate; halogen-containing ethylenically unsaturated compounds having 2 to 20 carbon atoms such as vinyl chloride, vinylidene chloride, vinylidene fluoride, tetrafluoroethylene and tetrachloroethylene; ethylenically unsaturated carboxylic acids having 3 to 20 carbon atoms such as acrylic acid, methacrylic acid, itaconic acid, maleic acid, fumaric acid, crotonic acid, citraconic acid, mesaconic acid, vinylacetic acid, allylacetic acid and vinylbenzoic acid (each of these acids may be in the form a salt such as an alkali metal salt (e.g. a sodium salt or a potassium salt), an ammonium salt or the like); ethylenically unsaturated carboxylic acid esters having 4 to 20 carbon atoms such as methyl methacrylate, ethyl methacrylate, propyl methacrylate, butyl methacrylate, 2-ethylhexyl methacrylate, lauryl methacrylate, stearyl methacrylate, vinyl methacrylate, allyl methacrylate, phenyl methacrylate, benzyl methacrylate, adamantyl methacrylate, tricyclodecanyl methacrylate, mentyl methacrylate, norbornyl methacrylate, isobornyl methacrylate, methyl acrylate, ethyl acrylate, butyl acrylate, 2-ethylhexyl acrylate, lauryl acrylate, stearyl acrylate, vinyl acrylate, adamantyl acrylate, tricyclodecanyl acrylate, mentyl acrylate, norbornyl acrylate, isobornyl acrylate, dimethyl itaconate, diethyl itaconate, dimethyl maleate, diethyl maleate, dimethyl fumarate, diethyl fumarate, methyl crotonate, ethyl crotonate, vinyl crotonate, dimethyl citraconate, diethyl citraconate, dimethyl mesaconate, diethyl mesaconate, methyl 3-buteoate, 2-hydroxyethyl methacrylate, 3-hydroxypropyl methacrylate, 2-hydroxypropyl methacrylate, 2-hydroxyethyl acrylate, 3-hydroxypropyl acrylate and 2-hydroxypropyl acrylate; cyano-containing ethylenically unsaturated compounds having 3 to 20 carbon atoms such as acrylonitrile, methacrylonitrile and allyl cyanide; ethylenically unsaturated amide compounds having 3 to 20 carbon atoms such as acrylamide, methacrylamide and maleimide; ethylenically unsaturated aldehydes having 3 to 20 carbon atoms such as acrolein and croton aldehyde; ethylenically unsaturated sulfonic acids having 2 to 20 carbon atoms such as vinylsulfonic acid and 4-vinylbenzene sulfonic acid (each of these acids may be in the form of a salt, for example, an alkali metal salt such as sodium salt and potassium salt); ethylenically unsaturated aliphatic amines having 2 to 20 carbon atoms such as vinylamine and allylamine; ethylenically unsaturated aromatic amines having 8 to 20 carbon atoms such as vinylaniline; ethylenically unsaturated aliphatic heterocyclic amines having 5 to 20 carbon atoms such as N-vinylpyrrolidone and vinylpiperidine; ethylenically unsaturated aromatic heterocyclic amines having 5 to 20 carbon atoms such as vinylpyridine and 1-vinylimidazole; ethylenically unsaturated alcohols having 3 to 20 carbon atoms such as allyl alcohol and crotyl alcohol; ethylenically unsaturated phenols having 8 to 20 carbon atoms such as 4-vinylphenol; and diene type compounds having 4 to 20 carbon atoms such as butadiene and isoprene.

The monomer unit shown by the general formula [15a] is originated from a monomer shown by the general formula [15]

[15]

(wherein G is an cyclic hydrocarbon residue containing a polymerizable double bond, and $R^{20}$ and $R^{21}$ have the same meaning as above).

The cyclic hydrocarbon residue shown by G' in the general formula [15a] is originated from the cyclic hydrocarbon residue containing a polymerizable double bond shown by G in the general formula [15], and the cyclic hydrocarbon containing a polymerizable double bond may be monocyclic or polycyclic and includes a cyclic hydrocarbon containing a polymerizable double bond having 6 to 12 carbon atoms, which is specifically exemplified, as preferable examples, by the followings.

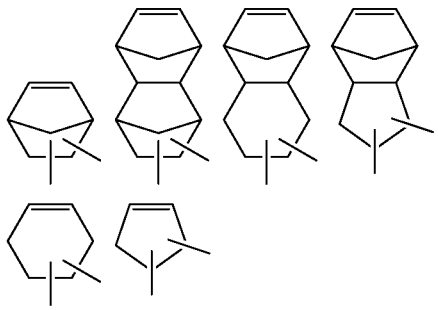

The alkyloxycarbonyl group shown by $R^{20}$ and $R^{21}$ in the general formulae [15] and [15a] may be straight chained or branched and includes one having 2 to 9 carbon atoms, which is specifically exemplified by a methyloxycarbonyl group, an ethyloxycarbonyl group, a propyloxycarbonyl group, a butyloxycarbonyl group, a pentyloxycarbonyl group, a hexyloxycarbonyl group, a heptyloxycarbonyl group, an octyloxycarbonyl group, a tert-butyloxycarbonyl group, 2-ethylhexyloxycarbonyl group, etc.

The group having hydrophilicity includes a hydroxyalkyloxycarbonyl group, a cyano group, a formyl group, a hydroxy group, a hydroxyalkyl group, a carboxyl group, a carboxyalkyl group, a carbamoyl group, a group of $-CH_2OCOCH_2COCH_3$, a group of $-CH_2OCOCH_2COC_2H_5$, a dicarboxyimido group ($-CO-NH-CO-$) formed by binding $R^{20}$ and $R^{21}$ with each other, etc.

The hydroxyalkyloxycarbonyl group includes one having 3 to 9 carbon atoms in which the hydrogen atom of the above alkyloxycarbonyl group is substituted by a hydroxy group, which is specifically exemplified by a hydroxyethyloxycarbonyl group, a hydroxypropyloxycarbonyl group, a hydroxybutyloxycarbonyl group, a hydroxypentyloxycarbonyl group, a hydroxyhexyloxycarbonyl group, a hydroxyheptyloxycarbonyl group, a hydroxyoctyloxycarbonyl group, etc.

The hydroxyalkyl group may be straight chained or branched and includes one having 1 to 8 carbon atoms, which is specifically exemplified by a hydroxymethyl group, a hydroxyethyl group, a hydroxypropyl group, a hydroxybutyl group, a hydroxypentyl group, a hydroxyhexyl group, a hydroxyheptyl group, a hydroxyoctyl group, etc.

The carboxyalkyl group may be straight chained or branched and includes one having 2 to 6 carbon atoms, which is specifically exemplified by a carboxymethyl group, a carboxyethyl group, a carboxypropyl group, a carboxybutyl group, a carboxypentyl group, etc.

The typical examples of the monomers shown by the general formula [15] specifically include the following

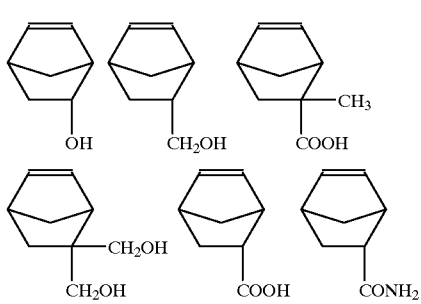

-continued

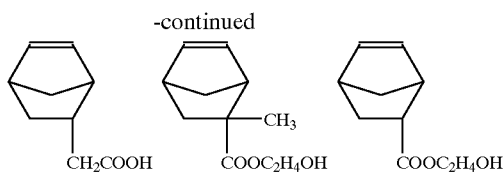

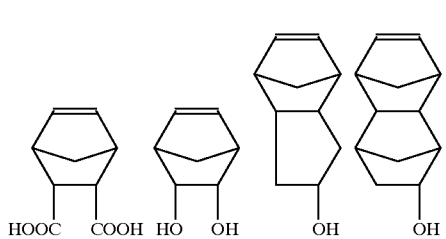

In the production of the polymer of the present invention, one or more of those monomer (hereinafter abbreviated as "other monomer") other than the monomer of the present invention may be co-used with the monomer of the present invention.

When the polymer of the present invention is used as a material for ArF resist composition, the monomer of the present invention and the "other monomer" co-used are preferably one having no aromatic group.

Further, in order to increase adhesion to a substrate, a monomer containing a group having hydrophilicity is preferably used and one containing a group having hydrophilicity and a cyclic hydrocarbon residue is more preferably used.

The polymer can generally be shown by the following general formula [20]

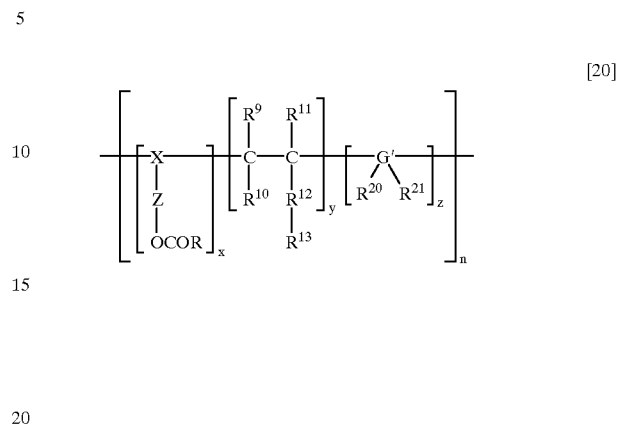

[20]

(letters x, y and z satisfy x+y+z=1, provided that $0.10 \leq x \leq 0.99$, $0 \leq y \leq 0.09$, $0 \leq z \leq 0.90$ and $0.01 \leq y+z \leq 0.90$; n is a degree of polymerization, and the remaining symbols have the same meaning as above).

and when the monomer unit shown by the general formula [13a] is possibly incorporated in the polymer chain, the polymer can be shown by the following general formula [20']

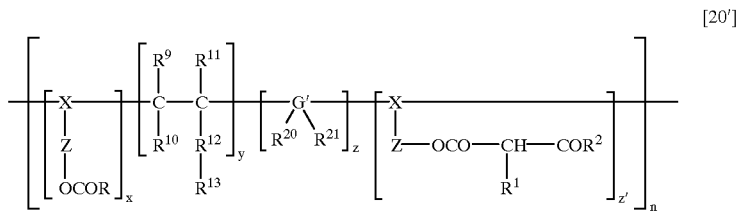

[20']

(letters x, y, z and z' satisfy x+y+z+z'=1, provided that $0.10 \leq x \leq 0.99$, $0 \leq y \leq 0.90$, $0 \leq z \leq 0.90$, $0 \leq z' \leq 0.50$ and $0.01 \leq y+z+z' \leq 0.90$; n is a degree of polymerization, and the remaining symbols have the same meaning as above).

Among the polymers, those shown by the following general formula [20"] are preferable

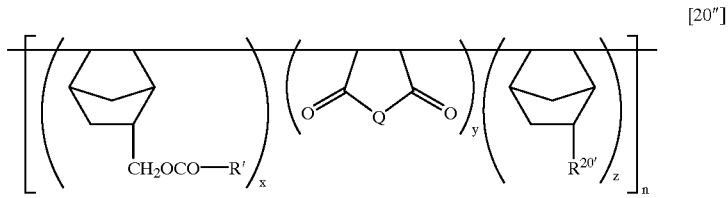

[20"]

(letters x, y and z satisfy x+y+z=1, provided that $0.10 \leq x \leq 0.99$, $0 \leq y \leq 0.90$, $0 \leq z \leq 0.90$ and $0.01 \leq y+z \leq 0.90$; n is a degree of polymerization, $R^{20'}$ is a hydroxy group or a hydroxymethyl group, Q has the same meaning as above and R' is a group shown by the following general formula [7], [8] or [8'])

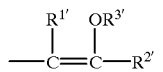

[7]

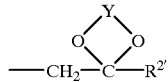

[8]

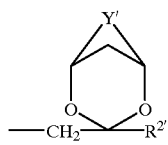

[8']

(wherein $R^{1'}$ is a hydrogen atom, $R^{2'}$ and $R^{3'}$ are a lower alkyl group having 1 to 4 carbon atoms and $R^{1'}$ and $R^{2'}$ may form together a lower alkylene group having 3 to 4 carbon atoms and Y and Y' are a group shown by the formula [9] or the general formula [9]

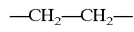

[9]

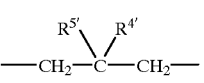

[10]

in which $R^{4'}$ and $R^{5'}$ are a hydrogen atom or a lower alkyl group having 1 to 4 carbon atoms).

The typical examples of the polymer of the present invention are those containing the following segment.

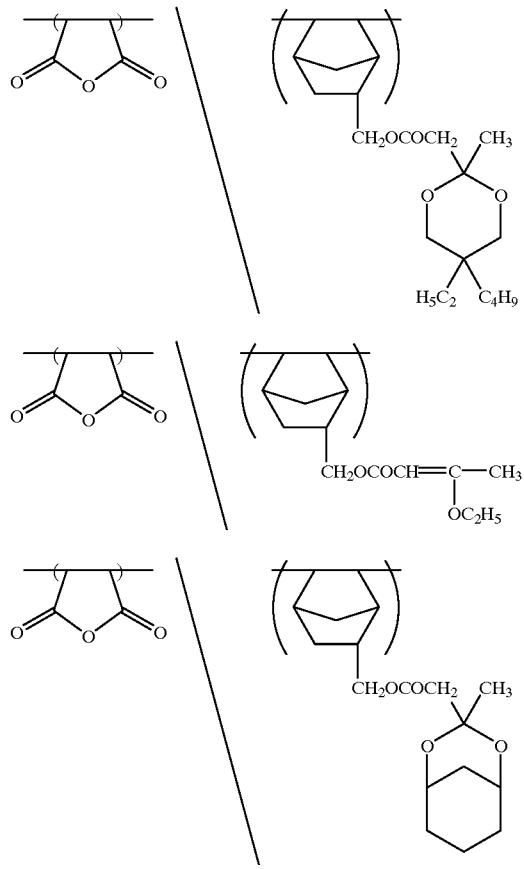

-continued
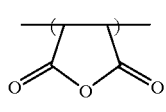 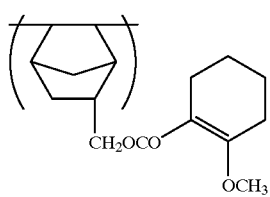
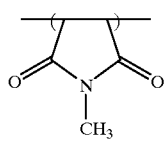 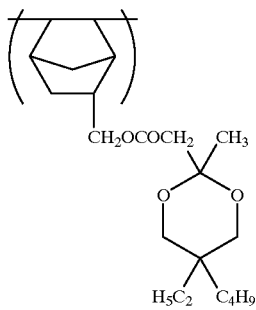
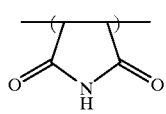 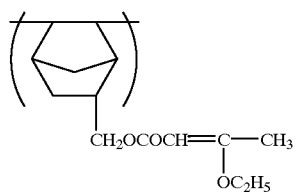
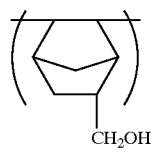 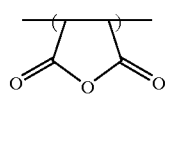 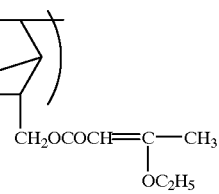
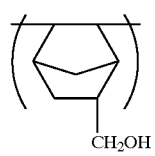 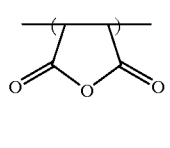 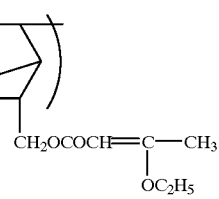
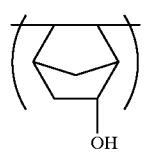 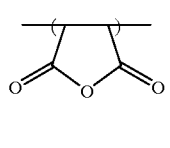 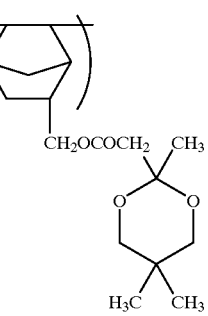

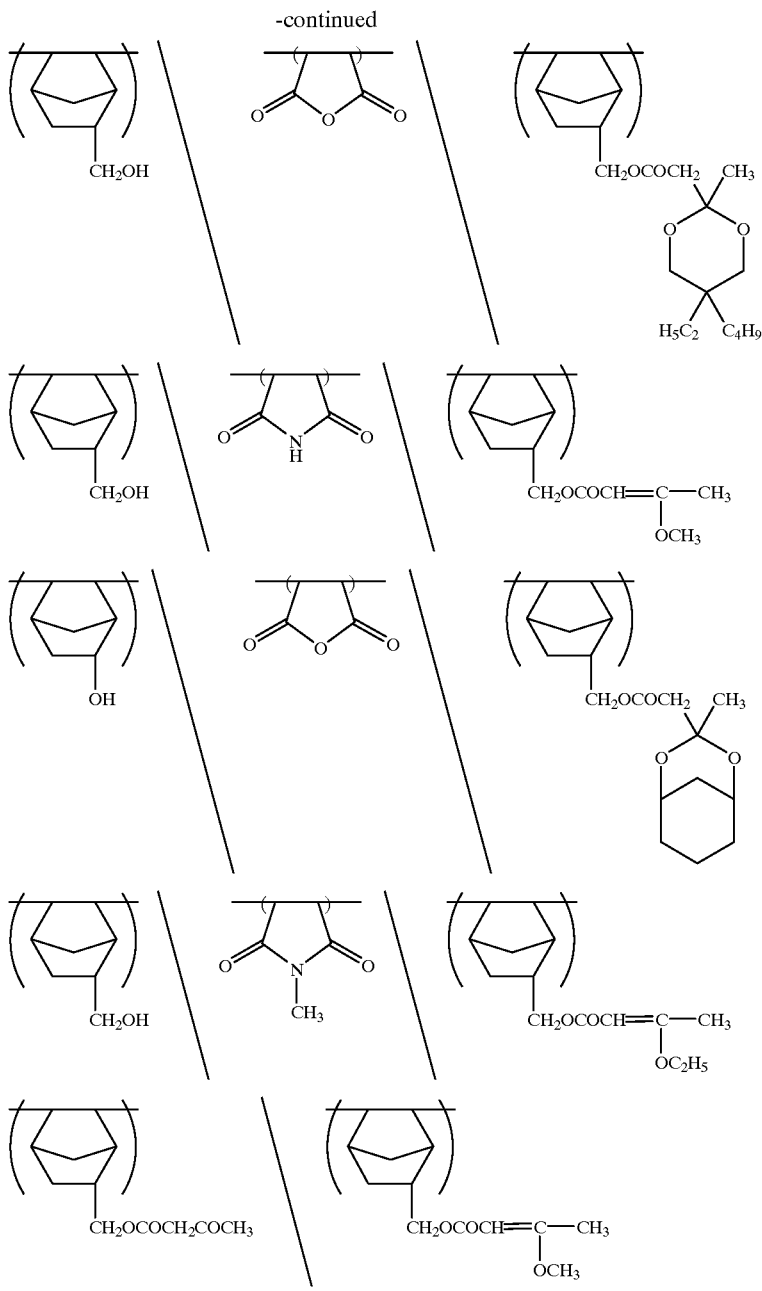

The polymer of the present invention can easily be produced by any one of the following methods (a) and (b).

(a) Method-1

The monomer of the present invention and, if necessary, "other monomer" are subjected to a polymerization reaction after conventional manner in a suitable solvent in the presence of a catalytic amount of a radical polymerization initiator, if necessary, under inert gas streams at 20 to 150° C. for 0.5 to 20 hours. After the reaction, after-treatment by a conventional manner in recovery of a polymer substance is conducted to give a polymer containing a monomer unit shown by the above general formula [1a] as a constituent unit.

The radical polymerization initiator includes an azo type polymerization initiator such as azobisisobutyronitrile, 2,2'-azobis(2,4-dimethylvaleronitrile), 2,2'-azobis(methyl 2-methylpropionate), 2,2'-azobis(2-methylbutyronitrile), 2,2'-azobis(2,4-dimethyl-4-methoxyvaleronitrile) and 4,4'-azobis(4-cyanopentanoic acid); a peroxide type polymerization initiator such as lauroyl peroxide, benzoyl peroxide, bis(4-tert-butylcyclohexyl)peroxydicarbonate, tert-butylperoxy-2-ethylhexanoate and methyl ethyl ketone peroxide, etc.

The reaction solvent is exemplified by organic solvent including a hydrocarbon such as benzene, toluene and xylene; an ester such as methyl acetate, ethyl acetate and n-butyl acetate; an ether such as ethyl ether, 1,2-dimethoxyethane, tetrahydrofuran, 1,4-dioxane and 1,3-dioxolane; an alcohol such as ethanol, n-propanol, isopropanol, n-butanol, sec-butanol, isobutanol and tert-butanol; a ketone such as methyl ethyl ketone, methyl isobutyl ketone and cyclohexanone, etc.

The inert gas used in the polymerization reaction under inert gas streams includes nitrogen gas, argon gas, etc.

(b) Method-2

The monomer of the present invention and, if necessary, "other monomer" are subjected to a polymerization reaction after conventional manner in a suitable organic solvent in the presence of a catalystic amount of an organic metal catalyst, if necessary, under inert gas streams at −78 to 50° C. for 0.5 to 48 hours. After the reaction, after-treatment by a conventional manner in recovery of a polymer substance is conducted to give a polymer containing a monomer unit shown by the above general formula [1a] as a constituent unit.

The organic metal catalyst includes an organic alkaline metal compound such as n-butyl lithium, sec-butyl lithium, tert-butyl lithium, sodium naphthalene, potassium naphthalene and cumyl potassium; an organic palladium compound such as $[Pd(CH_3CN)_4][BF_4]_2$, $[Pd(PhCN)_4][BF_4]_2$, $[Pd(C(CH_3)_3CN)_4][BF_4]_2$, $[Pd(C_5H_5N)_4][BF_4]_2$, $Pd(CH_3CN)_{4-n}(PPh_3)_n][BF_4]_2$ and $[Pd(CH_3CN)_x(CO)_y][BF_4]_2$.

The organic solvent includes an ether such as ethyl ether, 1,2-dimethoxyethane, tetrahydrofuran, 1,4-dioxane and 1,3-dioxolane; a ketone such as methyl ethyl ketone, methyl isobutyl ketone, acetone and cyclohexanone; an ester such as methyl acetate, ethyl acetate and n-butyl acetate; a hydrocarbon such as benzene, toluene and xylene; a nitro compound such as nitromethane and nitroethane, etc.

The organic solvent is preferably put into use under dried conditions.

The inert gas used in the polymerization reaction under inert gas streams includes nitrogen gas, argon gas, etc.

The concentrations of the monomer of the present invention and "other monomer" in the polymerization reaction are not specifically limited both in the above Method-1 and Method-2, and they are selected so that the total of the both monomers is generally 5 to 95 wt %, preferably 10 to 90 wt %.

The molecular weight of the polymer of the present invention containing the monomer unit shown by the general formula [1a] as the constituent unit is not specifically limited and generally 1,000 to 300,000, preferably 1,500 to 50,000, more preferably 1,500 to 30,000 in terms of weight-average molecular weight.

The degree of polymerization of the polymer of the present invention containing the monomer unit shown by the general formula [1a] as the constituent unit is not specifically limited and generally 4 to 2,000, preferably 8 to 500, more preferably 10 to 300.

The ratio of the monomer unit originated from the monomer of the present invention relative to that from "other monomer" in the copolymer obtained by using the both of the monomers is not specifically limited and generally 99 to 10 wt %, preferably 95 to 20 wt %.

The ratio of the monomer unit originated from "other monomer" in the copolymer is selected from a range of generally 1 to 90 wt %, preferably 5 to 80 wt %.

The characteristic feature of thus obtained polymer of the present invention lies in that it contains a substituted alkyl or alkenyl group having one or two protected hydroxy groups as substituent shown by the above general formula [5] or [6] in its molecule.

When the polymer of the present invention is used as a resist material, the protecting group in the substituted alkyl or alkonyl group haying one or two protected hydroxy groups as substituent shown by the above general formula [5] or [6] is released to give hydroxy groups by action of acid generated upon exposure, and the hydroxy groups of the resulting compound shows a similar pKa value (12 to 13) to one in a phenolic hydroxy group which is a soluble group in so far used novolac resin and phenol resin. Thus, by introducing the above substituted alkyl or alkenyl group in the polymer of the present invention, remarkable effects can be attained. Namely, the known alkaline developing solution, 2.38% aqueous TMAH solution can be used in the developing process after exposure, and therefore dissolving speed in an alkaline developing process can easily be controlled and further a resist material having excellent solubility can be provided.

Therefore, a resist composition comprising the above mentioned polymer of the present invention, a photosensitive compound generating acid upon exposure and a solvent dissolving those ingredients can effectively be used as a resist material for ArF excimer laser beams which is expected as an advanced exposure technology.

Upon using the polymer of the present invention for resist composition, the photosensitive compound which can generate an acid by exposure (hereinafter abbreviated as an photoacid generator) may be any one which can generate an acid by exposure and does not give any bad effect to a resist pattern formation, among which use are desirably made of those which show high transmittance around 193 nm and can keep high transparency of a resist composition and those which can enhance the transmittance around 193 nm by exposure and can keep high transparency of a resist composition.

Such photoacid generator particularly desirable in the present invention includes a sulfonium salt such as trimethylsulfonium.trifluoromethane sulfonate, triphenylsulfonium.trifluoromethane sulfonate, cyclohexylmethyl(2-oxocyclohexyl)sulfonium.trifluoromethane sulfonate, cyclopentylmethyl(2-oxocyclohexyl) sulfonium.trifluoromethane sulfonate and 2-oxocyclohexylmethyl(2-norbornyl) sulfonium.trifluoromethane sulfonate; a carboximide compound such as trifluoromethylsulfonyloxy-7-oxabicyclo[2.2.1]hept-5-ene-2,3-dicarboximide, trifluoromethylsulfonyloxy bicyclo[2.2.2]hept-5-ene-2,3-carboximide and trifluoromethylsulfonyloxy succinimide; a diazodisulfone compound such as 1-cyclohexylsulfonyl-1-(1,1-dimethylethylsulfonyl)diazomethane, bis(1,1-dimethylethylsulonyl)diazomethane, bis(1-methylethylsulfonyl)diazomethane, bis(cyclohexylsulfonyl) diazomethane, bis(isopropylsulfonyl)diazomethane, bis(tert-butylsulfonyl)diazomethane, tert-butylsulfonylmethylsuflonyl diazomethane and cyclohexylsulfonylethylsulfonyl diazomethane, etc.

As the above mentioned photoacid generator a commercially available one or one synthesized by a known method can be used.

The solvent used in the resist composition using the polymer of the present invention may be any of those which can dissolve the polymer of the present invention and the photoacid generator, and preferably those having good film-forming ability and having almost no absorbance at wavelength around 190 to 400 nm. Specific examples of the solvent are methyl Cellosolve acetate, ethyl Cellosolve acetate, propyleneglycol monomethyl ether acetate, propylenglycol monoethyl ether acetate, methyl lactate, ethyl lactate, 2-ethoxyethyl acetate, methyl pyruvate, ethyl pyruvate, methyl 3-methoxypropionate, ethyl 3-methoxypropionate, N,N-dimethylforamide, N,N-dimethylacetamide, N-methyl-2-pyrrolidone, cyclohexanone, methyl ethyl ketone, 2-heptanone, 1,4dioxane, diethyleneglycol monomethyl ether, diethyleneglycol dimethyl ether, ethyleneglycol monoisopropyl ether, etc.

The resist composition containing the polymer of the present invention is generally composed mainly of the above mentioned three components (the polymer of the present invention, the photoacid generator and the solvent), and if necessary, there may be incorporated therein an UV absorber [e.g. 9-diazofluorene and its derivative, 1-diazo-2-tetralone, 2-diazo-1-tetralone, 9-diazo-10-phenanthlone, benzophenone, 9-(2-methoxyethoxy)methylanthracene, 9-(2-ethoxyethoxy)methylanthracene, 9-(4-methoxybutoxy) methylanthracene, 9-anthracene methyl acetate, etc.].

Further, there may be incorporated therein suitable one or more of ingredients so far being used in this kind of technical field such as a sensitivity regulator [e.g. polyvinylpyridine, poly(vinylpyridine/methyl methacrylate), pyridine, piperidine, triethylamine, tri-n-propylamine, tri-n-butylamine, trioctylamine, tribenzylamine, dicyclohexylamine, dicyclohexylmethylamine, tetramethylammonium hydroxide, tetraethylammonium hydroxide, tetra-n-butylammonium hydroxide, N-methyl-2-pyrrolidone, etc.], a plasticizer [e.g. diethyl phthalate, diibutyl phthalate, dipropyl phthalate, etc.], an organic acid [e.g. salicylic acid, lactic acid, 2-hydroxynaphthalene-3-carboxylic acid, 2-nitrobenzoic acid, phthalic acid, succinic acid, malonic acid, etc.] and a surfactant [e.g. various commercially available nonionic surfactants, cationic surfactants, anionic surfactants and various kinds of fluorine type surfactants such as Fluorad (a trade name, mfd. by SUMITOMO 3M Co., Ltd.), EFTOP (a trade name, mfd. by TOHKEM PRODUCTS Corporation), SURFLON (a trade name, mfd. by Ashahi Glass Co., Ltd.), Ftergent (a trade name, mfd. by Neos Co. Ltd.), MEGAFAC (a trade name, mfd. by Dainippon Ink and Chemicals, Inc.), UNIDYNE (a trade name, mfd. by DAIKIN INDUSTRIES, LTD.),].

The pattern formation using the resist composition of the present invention can be conducted, for example, by the following.

The resist composition containing the polymer of the present invention is applied on the surface of a semiconductor substrate such as silicone wafer to form a layer having a thickness of 0.3 to 2.0 μm (when the layer is used as the top coating layer in three laminated layers, the thickness is 0.1 to 0.5 μm), and the resultant is subjected to prebaking in an oven at 70 to 130° C. for 10 to 30 minutes or on a hot plate at 60 to 150° C., preferably 60 to 110° C. for 60 to 180 seconds. Then, a mask for forming a desired pattern is placed over the above treated resist film and deep UV-lights having a wavelength of 220 nm or lower is irradiated thereon at a dose of 1 to 100 mJ/cm², followed by baking on a hot plate at 60 to 150° C., preferably at 60 to 110° C. for 60 to 180 seconds. Then, development is conducted with the use of a developing solution such as 0.1 to 5% aqueous tetramethylammonium hydroxide (TMAH) solution for 0.5 to 3 minutes after a dip method, a puddle method, a spray method and other conventional method, whereby the object pattern is formed on the substrate.

A ratio of the photoacid generator in the resist composition of the present invention to the polymer is such that 1 to 30 wt parts, preferably 1 to 20 wt parts of the photoacid generator is used relative to 100 wt parts of the polymer.

An amount of the solvent in the composition of the present invention is not specifically limited so far as a positive type resist material obtained by dissolving the polymer of the present invention and the photoacid generator in the solvent does not cause undesirable result when it is applied on a substrate, and generally 1 to 20 wt parts, preferably 1.5 to 10 wt parts, relative to 1 wt part of the polymer.

As the developing solution used in the above mentioned various kinds of methods for formation of a pattern, selection can be made of an aqueous alkaline solution having such a concentration as giving a large difference between solubility in an exposed part and one in a non-exposed part, generally having a concentration of 0.01 to 20%.

The aqueous alkaline solution used includes aqueous solutions containing an organic amine such as tetramethylammonium hydroxide (TMAH), tetraethylammonium hydroxide, tetrapropylammonium hydroxide, tetrabutylammonium hydroxide, choline, triethanolamine, morpholine and 1-methylmorpholine and an inorganic alkaline compound such as sodium hydroxide and potassium hydroxide.

The semiconductor substrate includes a silicone wafer, a polysilicone, a TiN substrate, a BPSG substrate, etc. The substrate is preferably treated previously with a substrate-treating agent such as hexamethyldisilazane (HMDS).

When the polymer of the present invention is used as a resist material, there can be attained such an excellent effect that pKa value can more suitably be selected as compared with conventional polymers so far being used for the same purpose and thus dissolving speed upon alkaline development can be controlled so that good resist pattern can be obtained, which makes it possible to manufacture higher integrated semiconductor devises such as semiconductor integrated circuits, this excellent effect being caused by the fact that the polymer of the present invention contains as a constituent unit a monomer unit shown by the general formula [1a] having a substituted alkyl or alkenyl group having one or two protected hydroxy groups as substituent shown by the general formula [5] or [6] as mentioned above.

The resist composition containing the polymer of the present invention is confirmed as showing a chemical amplification effect by virtue of an acid generated by irradiation with deep UV-lights, KrF excimer laser beams, electron beams and soft X-rays.

Therefore, the resist composition of the present invention is one which can form a pattern even after a method using irradiation with deep UV-lights, KrF excimer laser beams, electron beams and soft X-rays only in a low irradiation dose by utilizing this chemical amplification effect.

The following is specific explanation of the resist material containing the polymer of the present invention. Namely, in the part which is exposed by deep UV-lights having a wavelength of 220 nm or lower such as ArF excimer laser beams (λ=193 nm), an acid is generated according to the photo reaction shown by [equation 1], [equation 2] or [equation 3] mentioned below.

[equation 1]

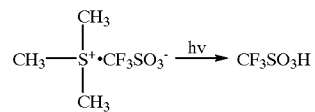

[equation 2]

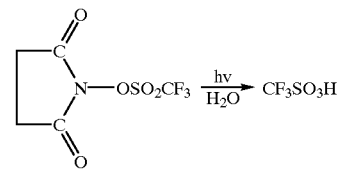

[equation 3]

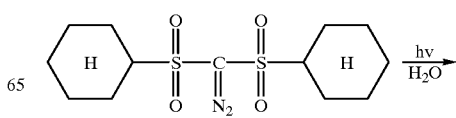

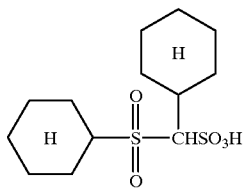

A heat treatment after the exposure process causes removing reaction on specific function groups of the polymer of the present invention according the following [equation 4] and [equation 5], whereby the polymer becomes alkaline soluble and thus it is dissolved in a developing solution upon development.

times, followed by drying over anhydrous magnesium sulfate. After removing the solvent by distillation, the resultant was distilled under reduced pressure by Vigoureux rectifying tube to give 118.4 g (yield 70%) of the object 5-norbornene-2-methyl acetoacetate as pale yellow oil.

$^1$H-NMR δ ppm (CDCl$_3$, 270 MHz): 0.56, 1.17 (m, 1H), 1.26 (d, 1H), 1.44 (d, 1H), 1.72–1.89 (m, 1H), 2.28 (s, 3H), 2.40 (m, 1H), 2.83 (s, 1H), 2.88 (s, 1H), 347 (s, 2H), 3.74, 4.05 (dd, 1H), 3.92, 4.22 (dd, 1H), 5.00 (s, 0.1H, enolated double bond 10%), 5.93–6.18 (m, 2H), 12.11 (s, 0.1H, enolated OH 10%).

Example 1

Synthesis of 5-norbornene-2-methyl 3-methoxy-2-butenoate

30 Grams (144.1 mmol) of 5-norbornene-2-methyl acetoacetate obtained in Reference Example 1 was dissolved

[Equation 4]

$$\{-O-\overset{O}{\underset{\|}{C}}-\overset{R^1}{\underset{|}{C}}=\overset{OR^3}{\underset{|}{C}}-R^2 \xrightarrow{H^+} \left[\{-O-\overset{O}{\underset{\|}{C}}-\overset{R^1}{\underset{|}{\underset{H}{C}}}-\overset{O}{\underset{\|}{C}}-R^2 \rightleftharpoons \{-O-\overset{O}{\underset{\|}{C}}-\overset{R^1}{\underset{|}{C}}=\overset{OH}{\underset{|}{C}}-R^2\right]$$

[Equation 5]

$$\{-O-\overset{O}{\underset{\|}{C}}-\overset{R^1}{\underset{|}{\underset{H}{C}}}-\overset{R^3O}{\underset{|}{\overset{OR^4}{C}}}-R^2 \xrightarrow{H^+} \left[\{-O-\overset{O}{\underset{\|}{C}}-\overset{R^1}{\underset{|}{\underset{H}{C}}}-\overset{O}{\underset{\|}{C}}-R^2 \rightleftharpoons \{-O-\overset{O}{\underset{\|}{C}}-\overset{R^1}{\underset{|}{C}}=\overset{OH}{\underset{|}{C}}-R^2\right]$$

On the other hand, in the part which is not exposed, no acid is generated, therefore no chemical change is caused even by the heat treatment.

Thus, in a case where a pattern formation is conducted with the use of the resist composition containing the polymer of the present invention, there is caused difference in solubility in the alkaline developing solution between exposed part and non-exposed part, and therefore a positive type pattern having high contrast can be formed.

In the following, the present invention is explained in more detail referring to Examples and Reference Examples, and the present invention is not limited thereto by any means.

The photoacid generator used in the Reference examples were synthesized by a method disclosed, for example, in Japanese Patent Application Kokai (Laid-Open) No. (JP-A-) 7-25846; T. M. Chapman et al, Synthesis, 1971, 591; T. M. Chapman et al, J.Org.Chem. 38, 3908(1973), etc.

EXAMPLE

Reference Example 1

Synthesis of 5-norbornene-2-methyl acetoacetate 100.30 Grams (807.7 mmol) of 5-norbornene-2-methanol (a mixture of endo-exo) was dissolved in 800 ml of toluene, and 0.82 g (8.1 mmol) of triethylamine was poured into the mixture, and then 67.9 g (807.7 mmol) of diketene was dropwisely added to the resultant at 30° C., through 15 minutes, followed by allowing a reaction to take place at room temperature with stirring for 4 hours. After keeping standing overnight, the reaction solution was washed with 260 ml of 1N-H$_2$SO$_4$ and then with 260 ml of water four in 47 ml (432.2 mmol) of methyl orthoformate, and 1.67 g (7.20 mmol) of camphor sulfonic acid was poured therein, followed by allowing a reaction to take place at room temperature with stirring for 3.5 hours. After keeping standing overnight, the reaction solution was diluted with 120 ml of toluene, and washed twice with 60 ml of saturated sodium bicarbonate solution, with 60 ml of water and with 60 ml of saturated sodium chloride solution in this order, followed by drying over anhydrous magnesium sulfate. After removing the solvent by distillation, the resultant crude product was distilled under reduced pressure to give 30.33 g (yield 94%) of the object 5-norbornene-2-methyl 3-methoxy-2-butenoate as pale yellow oil.

Boiling point:134–137° C./4 mmHg.

$^1$H-NMR δ ppm (CDCl$_3$, 270 MHz): 0.58, 1.17 (m, 1H), 1.26 (d, 1H), 1.45 (d, 1H), 1.80–1.90 (m, 1H), 2.29 (s, 3H), 2.38–2.43 (m, 1H), 2.82 (s, 1H), 2.90 (s, 1H), 3.64 (s, 3H), 3.66, 4.00 (dd, 1H), 3.86, 4.14 (dd, 1H), 5.03 (s,1H), 5.95–6.17 (m, 2H).

Example 2

Synthesis of 5-norbornene-2-methyl 3-ethoxy-2-butenoate 62.48 Grams (300 mmol) of 5-norbornene-2-methyl acetoacetate obtained in Reference Example 1 was dissolved in 150 ml (900 mmol) of ethyl orthoformate, and 3.48 g (15 mmol) of camphor sulfonic acid was poured therein, followed by allowing a reaction to take place at room temperature with stirring for 3.5 hours. After. keeping standing overnight, the reaction solution was diluted with 240 ml of toluene, and washed twice with 120 ml of saturated sodium bicarbonate solution, with 120 ml of water and with 120 ml of saturated sodium chloride solution in this order, followed by drying over anhydrous magnesium sulfate. After removing the solvent by distillation, the resultant crude product was distilled under reduced pressure to give 33.56 g (yield 47%) of the object 5-norbornene-2-methyl 3-ethoxy-2-butenoate as pale yellow oil.

Boiling point:128–132° C./4 mmHg.

$^1$H-NMR δ ppm (CDCl$_3$, 270 MHz): 0.57, 1.18 (m, 1H), 1.27 (d, 1H), 1.35 (t, J=6.96, 3H), 1.45 (d, 1H), 1.80–1.90 (m, 1H), 2.29 (s, 3H), 236–2.43 (m, 1H), 2.82 (s, 1H), 290 (s, 1H), 3.83 (q, J=6.96, 2H), 3.51, 3.98 (dd, 1H), 3.65, 4.13 (dd, 1H), 5.00 (s,1H), 5.94–6.17 (m, 2H).

Example 3

Synthesis of 5-norbornene-2-methyl- 2,2-(2',2'-dimethylpropylenedioxy)butanoate 52.07 Grams (250 mmol) of 5-norbornene-2-methyl acetoacetate obtained by a similar manner to Reference Example 1 was dissolved in 250 ml of toluene, and 78.11 g (750 mmol) of 2,2-dimethyl-1,3-propanediol and 0.48 g (2.5 mmol) of p-toluene sulfonic acid monohydrate were poured therein, followed by allowing a reaction to take place under refluxing with removing by-produced water by a water-separator for 4 hours. After the reaction was over, the reaction solution was washed with 125 ml of saturated sodium bicarbonate solution, 125 ml of water and 125 ml of saturated sodium chloride solution in this order, followed by drying over anhydrous magnesium sulfate. After removing the solvent by distillation, the resultant was distilled under reduced pressure to give 45.86 g (yield 62.3%) of the object 5-norbornene-2-methyl-2,2-(2',2'-dimethylpropylenedioxy) butanoate as pale yellow oil.

Boiling point: 141–147° C./3 mmHg.

$^1$H-NMR δ ppm (CDCl$_3$, 270 MHz): 0.52–0.59, 1.12–1.18 (m, 1H), 0.94 (s, 3H), 1.01 (s 3H), 1.25 (d, 1H), 1.45 (d, 1H), 1.46 (s, 3H), 1.79–1.88 (m, 1H), 2.38–2.43 (m, 1H), 2.80 (d, 3H), 2.89 (s, 1H), 3.48–4.13 (m, 6H), 5.92–6.17 (m, 2H).

Example 4

Synthesis of 5-norbornene-2-methyl 2,2-(2'-butyl-2'-ethyl propylenedioxy)butanoate 24.99 Grams (120 mmol) of 5-norbornene-2-methyl acetoacetate obtained by a similar manner to Reference Example 1 was dissolved in 240 ml of toluene, and 28.85 g (180 mmol) of 2-butyl-2-ethyl-1,3-propanediol and 1.39 g (6 mmol) of dl-camphor sulfonic acid were poured therein, followed by allowing a reaction to take place under refluxing with removing by-produced water by a water-separator for 5 hours. After the reaction was over, the reaction solution was washed with 60 ml of saturated sodium bicarbonate solution, 60 ml of water and 60 ml of saturated sodium chloride solution in this order, followed by drying over anhydrous magnesium sulfate. After removing the solvent by distillation, the resulting crude product was purified by column chromatography [packing: WakoGel C-200 (Trade Name of Wako Pure Chemical Industries, Ltd.); eluent: n-hexane/ethyl acetate=4/1] to give 32.95 g (yield 78.3%) of the object 5-norbornene-2-methyl 2,2-(2'-butyl-2'-ethylpropylenedioxy)butanoate as pale yellow oil.

$^1$H-NMR δ ppm (CDCl$_3$, 270 MHz): 0.53–0.60 (m, 1H), 0.77–0.84 (m, 3H), 0.91 (t, J=6.96, 3H), 1.11–1.51 (m, 10H), 1.54(s 3H), 1.79–1.88 (m, 1H), 2.36–2.45 (m, 1H), 2.81–2.78 (m, 3H), 2.89 (s, 1H), 3.54–4.19 (m, 6H), 5.92–6.17 (m, 2H).

Example 5

0.40 Gram (3.2 mmol) of 5-norbornene-2-methanol (endo-exo mixture), 2.98 g (30,4 mmol) of maleic anhydride, 10.31 g (46.4 mmol) of 5-norbornene-2-methyl 3-methoxy-2-butenoate obtained in Example 1 and 44 ml of dried tetrahydrofuran (THF) were mixed with each other. The mixture was heated at 65° C. and 0.53 g (3.2 mmol) of azobisisobutylonitrile was added thereto, followed by allowing a polymerization reaction to take place at the same temperature under nitrogen streams for 16 hours. After the reaction was over, the reaction solution was poured into 500 ml of n-hexane to precipitate a polymer. The polymer was recovered by filtration and dried to give 5.93 g (yield 43%) of the object product. The constituent ratio of 5-norbornene-2-methanol unit/maleic anhydride unit/5-norbornene-2-methyl 3-methoxy-2-butenoate unit was found to be about 0.16/0.33/0.50 by $^1$H-NMR measurement, and the weight-average molecular weight (Mw) and dispersity thereof were found to be 2000 and 1.50, respectively by GPC (gel permeation chromatography, solvent:tetrahydrofuran) using polystyrene as a standard.

Example 6

The same polymerization reaction as Example 5 was conducted except for using 5-norbornene-2-methyl 3-ethoxy-2-butenoate obtained in Example 2 in place of 5-norbornene-2-methyl 3-methoxy-2-butenoate to give 5.75 g (yield 40%) of the object product. The constituent ratio of 5-norbornene-2-methanol unit/maleic anhydride unit/5-norbornene-2-methyl 3-ethoxy-2-butenoate unit was found to be about 0.16/0.33/0.50 by $^1$H-NMR measurement, and the weight-average molecular weight (Mw) and dispersity thereof were found to be 2300 and 1.48, respectively by GPC (gel permeation chromatography, solvent:tetrahydrofuran) using polystyrene as a standard.

Example 7

The same polymerization reaction as Example 5 was conducted except for using 5-norbornene-2-methyl 2,2-(2',2'-dimethylpropylenedioxy) butenoate obtained in Example 3 in place of 5-norbornene-2-methyl 3-methoxy-2-butenoate to give 6.48 g (yield 38%) of the object product. The constituent ratio of 5-norbornene-2-methanol unit/maleic anhydride unit/5-norbornene-2-methyl 2,2-(2',2'-dimethylpropylenedioxy) butenoate unit was found to be about 0.16/0.33/0.50 by $^1$H-NMR measurement, and the weight-average molecular weight (Mw) and dispersity thereof were found to be 2000 and 1.50, respectively by GPC (gel permeation chromatography, solvent:tetrahydrofuran) using polystyrene as a standard.

Example 8

The same polymerization reaction as Example 5 was conducted except for using 5-norbornene-2-methyl 2,2-(2'-butyl-2'-ethylpropylenedioxy) butenoate obtained in Example 4 in place of 5-norbornene-2-methyl 3-methoxy-2-butenoate to give 6.69 g (yield 34%) of the object product. The constituent ratio of 5-norbornene-2-methanol unit/ maleic anhydride unit/5-norbornene-2-methyl 2,2-(2'-butyl-2'-ethylpropylenedioxy) butenoate unit was found to be about 0.16/0.33/0.50 by $^1$H-NMR measurement, and the weight-average molecular weight (Mw) and dispersity thereof were found to be 2500 and 1.29, respectively by GPC (gel permeation chromatography, solvent:tetrahydrofuran) using polystyrene as a standard.

Example 9

0.09 Gram (0.2 mmol) of [Pd(CH$_3$CN)$_4$][BF$_4$]$_2$ was suspended in 15 ml of nitromethane., and then a solution containing 1.25 g (6 mmol) of 5-norbornene-2-methyl acetoacetate obtained in Reference Example 1, 3.11 g (14 mmol) of 5-norbornene-2-methyl 3-methoxy-2-butenoate obtained in Example 1 and 5 ml of nitromethane was dropwisely added to the suspension minutes at room temperature through 5 minutes under nitrogen gas streams, followed by allowing a polymerization reaction to take place at room temperature for 16 hours. After the reaction was over, the polymerization catalyst was removed by filtration, the filtrate was poured into 200 ml of diisopropylether (IPE) to precipitate a polymer. The polymer was recovered by filtration and dried to give 1.98 g (yield 45%) of the object product. The constituent ratio of 5-norbornene-2-methyl acetoacetate unit/5-norbornene-2-methyl 3-methoxy-2-butenoate unit was found to be about 0.30/0.70 by $^1$H-NMR measurement, and the weight-average molecular weight (Mw) and dispersity thereof were found to be 19200 and 2.27, respectively by GPC (gel permeation chromatography, solvent:tetrahydrofuran) using polystyrene as a standard.

Reference Example 2

A resist composition comprising the following ingredients was prepared.

| | | |
|---|---|---|
| (a) | the polymer obtained in Example 5 | 3.0 g |
| (b) | a photoacid generator (triphenylsulfonium trifluoromethanesulfonate) | 60 mg |
| (c) | ethylene glycol dimethyl ether | 15.6 g |

The above resist composition was filtered by 0.1 μm Tefron filter and the filtrate was spin-coated on a silicone wafer, followed by baking on a hot plate at 140° C. for 60 seconds to give a resist film of 0.4 μm thick.

The wafer having the film formed was placed in a sufficiently purged Stepper by nitrogen and ArF excimer laser beams (λ=193 nm; NA 0.55) was irradiated thereon through a mask having a pattern, followed by heating on a hot plate at 90° C. for 60 seconds, and the resultant was subjected to development using a developing solution [2.38% TMAH aqueous solution at 23° C.] by a puddle method for 60 seconds, followed by rinsing treatment using ultra pure water for 60 seconds to give 0.17 μm (exposure dose about 36 mJ/cm$^2$) line and space pattern.

As explained above, the present invention provides a novel polymer useful for a resist composition, etc. utilized in the production of semiconductor elements, etc. and a novel monomer useful as a starting material for the polymer, and a resist composition using the polymer of the present invention can remarkably advantageously be used as a resist material for ArF excimer laser beams which has been considered to be a valuable technology for exposure belonging to the coming generation. Thus, the present invention has a great value for formation of fine pattern in semiconductor industries, etc.

Further, the polymer of the present invention has a chelating ability and therefore is expected to be useful in analyticals, purification of metals, etc. as a functional resin for analysis and separation.

What is claimed is:

1. A polymer, which contains, as a structural unit, a monomer unit shown by the general formula [1a]

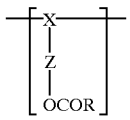

[1a]

(wherein X is a cyclic hydrocarbon residue which may have a substituent, Z is a spacer or a direct bond, and R is a substituted alkyl or alkenyl group having one or two protected hydroxyl groups as substituent).

2. A polymer as claimed in claim 1, wherein the cyclic hydrocarbon residue which may have a substituent, shown by X in the general formula [1a] is a group shown by any one of the general formulae [2a] to [4a]

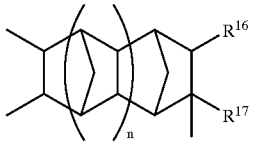

[2a]

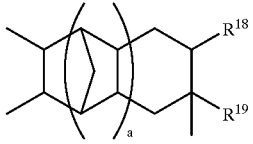

[3a]

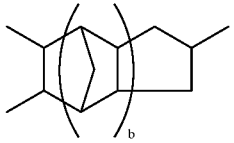

[4a]

(wherein R$^{16}$ to R$^{19}$ are each independently a hydrogen atom, an alkyl group, a cyano group, an alkyloxycarbonyl group, an aryl group, an aralkyl group or a carbamoyl group, and n, a and b are 0 or 1).

3. A polymer as claimed in claim 1 or claim 2, wherein the substituted alkyl or alkenyl group, shown by R in the general formula [1a] is a group shown by the general formula [5]

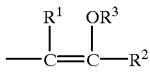

[5]

(wherein R$^1$ and R$^2$ are each independently a hydrogen atom, an alkyl group, a substituted alkyl group or an alicyclic hydrocarbon residue, and R$^1$ and R$^2$ may form together an aliphatic ring, and R$^3$ is an alkyl group, an alkenyl group, a hydroxyalkyl group, an alkyloxycarbonyl group or an alkylsilyl group) or a group shown by the general formula [6]

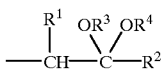

[6]

(wherein R$^4$ is an alkyl group and R$^1$, R$^2$ and R$^3$ have the same meaning as above, and R$^3$ and R$^4$ may form together an aliphatic ring).

4. A polymer as claimed in claim 1, wherein the substituted alkyl or alkenyl group, shown by R is a group shown by the following general formula [7], [8] or [8']

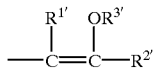 [7]

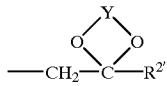 [8]

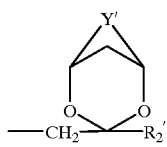 [8']

(wherein $R^{1\prime}$ is a hydrogen atom, $R^{2\prime}$ and $R^{3\prime}$ are a lower alkyl group having 1 to 4 carbon atoms and $R^{1\prime}$ and $R^{2\prime}$ may form together a lower alkylene group having 3 to 4 carbon atoms and Y and Y' are a group shown by the formula [9] or the general formula [10]

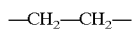 [9]

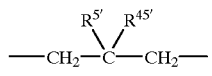 [10]

in which $R^{4\prime}$ and $R^{5\prime}$ are a hydrogen atom or a lower alkyl group having 1 to 4 carbon atoms).

5. A polymer as claimed in claim 1 or 2 wherein the spacer is a group shown by the general formula [11]

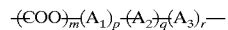 [11]

(wherein $A_2$ is a divalent hydrocarbon residue which may contain an oxygen atom, $A_1$ and $A_3$ are each independently a lower alkylene group, m, p, q and r are each independently 0 or 1, provided that q is 1 when m is 1, and at least one of m, p, q and r is 1).

6. A polymer as claimed in claim 5, wherein the spacer shown by the general formula [11] is group shown by the general formula [12]

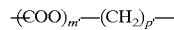 [12]

(wherein m' and p' are each independently 0 or 1, provided that at least one of m' and p' are 1).

7. A polymer as claimed in claim 2, wherein $R^{16}$ to $R^{19}$ are a hydrogen atom.

* * * * *